US010076561B2

(12) United States Patent
Gonzalez Gonzalez et al.

(10) Patent No.: US 10,076,561 B2
(45) Date of Patent: Sep. 18, 2018

(54) **VECTORS FOR TRANSFORMING *MYCOPLASMA HYOPNEUMONIAE*, TRANSFORMED *M. HYOPNEUMONIAE* STRAINS, AND USE THEREOF**

(71) Applicant: HIPRA SCIENTIFIC, S.L.U., Amer (ES)

(72) Inventors: Luis Gonzalez Gonzalez, Badalona (ES); Jaume Piñol Ribas, Valldoreix (ES); Jordi Montane Giralt, Sant Feliu de Pallerols (ES); Maria Camats Malet, Barcelona (ES); Enrique Querol Murillo, Barcelona (ES); Marta Sitja Arnau, Girona (ES)

(73) Assignee: HIPRA SCIENTIFIC, S.L.U., Amer (ES)

( * ) Notice: Subject to any disclaimer, the term of this patent is extended or adjusted under 35 U.S.C. 154(b) by 0 days.

(21) Appl. No.: 14/413,946

(22) PCT Filed: Jul. 9, 2013

(86) PCT No.: PCT/ES2013/070492
§ 371 (c)(1),
(2) Date: Jun. 5, 2015

(87) PCT Pub. No.: WO2014/009586
PCT Pub. Date: Jan. 16, 2014

(65) Prior Publication Data
US 2015/0306200 A1 Oct. 29, 2015

(30) Foreign Application Priority Data
Jul. 10, 2012 (EP) .................................... 12382277

(51) Int. Cl.

| | |
|---|---|
| ***A61K 39/02*** | (2006.01) |
| ***C12N 15/74*** | (2006.01) |
| ***C12N 1/00*** | (2006.01) |
| ***C12N 15/00*** | (2006.01) |
| ***C12N 15/63*** | (2006.01) |
| ***C12N 15/64*** | (2006.01) |
| ***C12R 1/35*** | (2006.01) |
| ***C12N 1/20*** | (2006.01) |
| *A61K 39/00* | (2006.01) |

(52) U.S. Cl.
CPC ............ *A61K 39/0241* (2013.01); *C12N 1/20* (2013.01); *C12N 15/00* (2013.01); *C12N 15/63* (2013.01); *C12N 15/64* (2013.01); *C12N 15/74* (2013.01); *C12R 1/35* (2013.01); *A61K 2039/522* (2013.01); *A61K 2039/552* (2013.01); *C12N 2800/70* (2013.01); *C12N 2820/55* (2013.01)

(58) Field of Classification Search
None
See application file for complete search history.

(56) References Cited

FOREIGN PATENT DOCUMENTS

| | | |
|---|---|---|
| WO | WO 2009/061798 | 8/2009 |
| WO | WO 2010/132932 | 11/2010 |

OTHER PUBLICATIONS

"Development of genetic manipulation protocols for Mycoplasma Hyopneumoniae Clade of animal Pathogens", University of Missouri, 3 pgs. (http://www.reeis.usda.gov/web/crisprojectpages/0220630-development-of-genetic-manipulation-protocols-for-mycoplasma-hyopneumoniae-clade-of-animal-pathogens.html, accessed 2/162012).
Ausubel et al., "Current Protocols in Molecular Biology", vol. 1, John Wiley and Sons, Inc (1999), title page and table of contents.s.
Browning et al., "Developing attenuated vaccines to control mycoplasmoses", Microbiology Australia, pp. 121-122 (2011).
Cao et al., "Transformation of Mycoplasma gallisepticum with Tn916, Tn4001, and Integrative Plasmid Vectors", J. of Bacteriology vol. 173, No. 14, pp. 4459-4462 (1994).
Caron et al., "Diagnosis and Differentiation of *Mycoplasma hyopneumoniae* and *Mycoplasma hyorhinis* Infections in Pigs by PCR Amplification of the p36 and p46 Genes", J. of Clin. Microbiol. vol. 38, No. 4, pp. 1390-1396 (2000).
Chow et al., Aminoglycoside Resistance Genes aph (2")-lb and aac (6')-Im Detected Together in Strains of both *Escherichia coli* and *Enterococcus faecium*, Antimicrob. Agents Chemother. vol. 45, No. 10, pp. 2691-2694 (2001).
Christensen et al., "Diseases of the respiratory system" Diseases of Swine. 8$^{a}$ Edición. Straw B.E., D'Allaire S., Mengelimg W.L. and Taylor D.J. Iowa State University Press, Ames (IA) 1999, p. 914.
Dybvig et al., "Construction and Use of Derivatives of Transposon Tn 4001 That Function in Mycoplasma pulmonis and Mycoplasma arthritidis", J. of Bacteriology 182 (15), pp. 4343-4347 (2000).
Fort et al., "Porcine circovirus type 2 (PCV2) Cap and Rep proteins are involved in the development of cell-mediated immunity upon PCV2 infection", Vet. Immunology Immunopathology 137, pp. 226-234 (2010).

(Continued)

*Primary Examiner* — Oluwatosin A Ogunbiyi
(74) *Attorney, Agent, or Firm* — Squire Patton Boggs (US) LLP

(57) ABSTRACT

The present invention relates to mutant strains of *Mycoplasma hyopneumoniae* and to a method for preparing them. It also relates to carrier vectors which are used in said method, to vaccine compositions and to vaccination kits comprising the compositions against porcine enzootic pneumonia and other swine diseases. It also relates to the use of *M. hyopneumoniae* as a host for expressing recombinant proteins and other DNA sequences of interest.

46 Claims, 10 Drawing Sheets

Specification includes a Sequence Listing.

(56) References Cited

OTHER PUBLICATIONS

Gennaro, "Remington: The Science and Practice of Pharmacy", 20th Ed., Lippincott Willimas & Wilkins, Philadelphia (2000), Title page and table of contents.
Halbedel et al. "Tools for the genetic analysis of *Mycoplasma*", International Journal of Medical Microbiology, vol. 297, No. 1, pp. 3-44 (2007).
Hedreyda et al., "Transformation of *Mycoplasma pneumoniae* with Tn4001 by Electroporation", Plasmid, New York, vol. 30, No. 2, pp. 170-175 (1993).
International Preliminary Report on Patentability for PCT ES2013/070492, dated Jan. 13, 2015, 18 pgs.
International Search Report and Written Opinion for PCT/ES2013/070492, dated Apr. 24, 2014, 28 pgs.
Lartigue et al., "Host specificity of mollicutes oriC plasmids: functional analysis of replication origin", Nucleic Acids Research vol. 31, No. 22, pp. 6610-6618 (2003).
Lee et al., "Development of a replicable oriC plasmid for *Mycoplasma gallisepticum* and *Mycoplasma imitans*, and gene disruption through homologous recombination in *M. gallisepticum*", Microbiology, vol. 154, No. 9, pp. 2571-2580 (2008).
Maboni Siqueira et al., "Mycoplasma hyopneumoniae Transcription Unit Organization: Genome Survey and Prediction", DNA Research 18, pp. 413-422 (2011).
Madsen et al., "Transcriptional Profiling of *Mycoplasma Hyopneumonia* During Heat Schock Using Microarrays", Infect. Immun. 74(1), pp. 160-166 (2006).
Minion el al., "The Genome Sequence of *Mycoplasma hyopneumoniae* strain 232, the Agent o Swine Mycoplasmosis", J. of Bacteriology 186 (21); pp. 7123-7133 (2004).
Olvera et al., "Comparison of porcine circovirus type 2 load in serum quantified by a real time PCR in postweaning multisystemic wasting syndrome and porcine dermatitis and nepropathy syndrome naturally affected pigs", J. of Virological Methods 117, pp. 75-80 (2004).
Pich et al., "Comparative analysis of antibiotic resistance gene markers in *Mycoplasma genitalium*: application to studies of the minimal genes complement", Microbiology 152, pp. 519-527 (2006).
Quintana et al., "Clinical and pathological observations on pigs with postweaning multisystemic wasting syndrome", Veterinary Record vol. 149, pp. 357-361 (2001).
Reddy et al., "Isolation and characterization of transposon Tn4001-generated, cytadherence-deficient transformants of Mycoplasma pneumoniae and Mycoplasma genitalium", Fems Immunology and Medical Microbiology, vol. 15, No. 4, pp. 199-211 (1996).
Rowe et al., "Handbook of Pharmaceutical Excipients", 4th edition, Phramaceutical Press, London, (2003), title page and table of contents.
Sambrook and Russell, Molecular Cloning 3rd Ed. Cold Spring Harbor Laboratory Press, Cold Spring Harbor New York, Title pg. and Table of contents (2001).
Terra Lopes "Construção De Vetor OriC De *Mycoplasma Hyopneumoniae*—Uma Ferramenta Para Estudos Geneticos Do Agente Da Pneumonia Enzoótica Suína", LUME—Disertation work, Digital Repository of the Universidade Federal do Rio Grande do Sul XP002689217, Porto Alegre, 64 pgs. (2007), Retrieved from the Internet: URL:http://www.lume.ufrgs.br/bitstream/han.
Terra Lopes, "Construction of a *Mycoplasma hyopneumoniae* oriC vector-a tool for genetic studies on the suine enzootic pneumonia agent", Acta Scientiae Veterinariae vol. 37, No. 1 p. 112 (2009).
Vasconcelos et al., "Swine and poultry pathogens: the complete genome sequences of two strains of Mycoplasma hyopneumoniae and a strain of Mycoplasma synoviae", J. of Bacteriology, vol. 187, No. 16, pp. 5568-5577 (2005).
Weber, Shana De Souto et al., "Unveiling Mycoplasma hyopneumoniae Promoters: Sequence Definition and Genomic Distribution", DNA Research, vol. 19, No. 2, pp. 103-115 (2012).
Zimmerman et al., "Synthesis of a small, cysteine-rich, 29 amino acids long peptide in *Mycoplasma pneumoniae*", FEMS Microbiology Letters, vol. 253, No. 2, pp. 315-321 (2005).
Sernova et al. "Identification of replication origins in prokaryotic genomes," Briefings in Bioinformatics, 2008, vol. 9, No. 5, pp. 376-391.

A

B

| | 6314Cc1 | 232Cc6 | 232Lc2 | 232Tc2 | C+ | C- |
|---|---|---|---|---|---|---|
| 1/2 Dilution | - | - | 1,147 | | 1,479 | 0,109 |
| 1/25 Dilution | - | - | 0,19 | 1.672 | | |
| 1/50 Dilution | - | - | - | - | | |
| 1/100 Dilution | - | - | - | 0,612 | | |
| 1/250 Dilution | 0,753 | 0,154 | - | - | | |
| 1/500 Dilution | 0.123 | 0,079 | - | - | | |

C

VECTORS FOR TRANSFORMING *MYCOPLASMA HYOPNEUMONIAE*, TRANSFORMED *M. HYOPNEUMONIAE* STRAINS, AND USE THEREOF

CROSS-REFERENCE TO RELATED APPLICATIONS

This application is the National Stage of International Patent Application No. PCT/ES2013/070492, filed Jul. 9, 2013, which claims the benefit of EP Application No. 12382277.7, filed Jul. 10, 2012, each of which is incorporated by reference in its entirety.

TECHNICAL FIELD

The present invention is comprised in the field of the development of methods and tools for the genetic manipulation of *Mycoplasma hyopneumoniae* for the purpose of preparing transformed mutant strains of said bacterial species which can be used as vaccines against porcine diseases.

BACKGROUND ART

In the veterinary field, diseases caused by microorganisms such as bacteria, viruses or parasites cause serious economic losses due to death of the animals, or due to a low performance in the growth and fattening processes.

One of the ways to protect animals against future infections consists of the administration of vaccines to generate an immunological response.

Vaccines based on inactivated microorganisms or live attenuated microorganisms have been the main immunological basis for the control and eradication of most infectious diseases up until now.

However, despite the good results obtained with these types of vaccines, they present problems such as the possible reversion to the virulence of attenuated vaccines, the inability to differentiate vaccinated animals from infected animals or the difficulty of achieving a vaccine that is effective for all diseases.

The development of tools for the genetic manipulation of microorganisms has typically allowed preparing vaccines that are more effective than those mentioned above, such as for example, subunit vaccines, genetically modified inactivated or live vaccines, marker vaccines (DIVA) or DNA vaccines.

Nevertheless, not all the disease-causing microorganisms in the veterinary field can be easily genetically manipulated.

Mycoplasmas are among the microorganisms difficult to be manipulated at the genetic level.

Mycoplasmas belong to the Mollicutes class, a wide group of microorganisms closely related with Gram positive bacteria.

Mycoplasmas have small circular genomes with sizes generally smaller than 1,000 kb, with a number of genes ranging between 500 and 1000.

This group of bacteria also lacks many of the metabolic pathways that are usually found in all living organisms, probably as a result of their adaptation to a parasitic lifestyle. In consequence, mycoplasmas are fastidious microorganisms that are very difficult to culture both in liquid and in solid medium.

Mycoplasmas include *Mycoplasma hyopneumoniae* (hereinafter, "Mhyo"), which is a bacterium responsible for huge economic losses in the porcine industry. Although most Mhyo infections are not severe, animals infected by Mhyo are predisposed to secondary infections of the respiratory system that can reduce the daily weight gain rate or even cause death.

Mhyo is the causative agent of porcine enzootic pneumonia (hereinafter "PEP"), a very widespread worldwide chronic respiratory disease. The disease is characterized by high morbidity and low mortality. The prevalence of PEP is particularly high in fattening pigs and the severity of the clinical signs depends on strain of Mhyo causing the infection, on environmental conditions, on the health condition of the animals and on the onset of secondary infections due to other pathogenic agents. In some cases, PEP presents in a sub-clinical manner without evident clinical signs. In cases where there are no complications, the animals show a chronic, non-productive cough associated with a reduced daily weight gain rate, with the subsequent reduction of the feed conversion efficiency. When secondary infections occur, the clinical signs become more evident, presenting acute respiratory symptoms and pyrexia, which can even cause the death of the animal. Nevertheless, even in the absence of complications due to secondary infections, PEP causes serious economic losses due to the low feed conversion rates and the costs derived from medication. Once the disease is established on a farm, it is transmitted horizontally to other animals by means of the cough-generated aerosols and vertically from the reproductive females to the piglets.

In addition to problematic culturing, the genetic manipulation of mycoplasmas is hindered because of the few tools available.

The difficulties in the genetic manipulation of mycoplasmas, particularly of Mhyo, have been described in the state of the art.

The genome sequence of Mhyo strain 232 is described in the article by Minion et al., *The Genome Sequence of Mycoplasma hyopneumoniae Strain* 232, *the Agent of Swine Mycoplasmosis*, J. Bacteriol., 2004, 186(21), 7123-7133. The author states that Mhyo is a fastidious microorganism and that there is a lack of tools and protocols for transforming it.

In the context of the study of modifications occurring in Mhyo when subjected to a temperature change, in the article by Madsen et al., *Transcriptional Profiling of Mycoplasma hyopneumoniae during Heat Shock Using Microarrays*, Infect. Immun., 2006, 74(1), 160-166, the authors state that despite the huge importance of Mhyo in porcine production, there have been few studies on the potential molecular mechanisms of its pathogenesis in response to environmental changes, and that this is probably due to its growth difficulties and due to the fact that it is a microorganism refractory to genetic manipulation.

In the article by Pich et al., *Comparative analysis of antibiotic resistance marker genes in Mycoplasma genitalium: application to studies of the minimal gene complement*, Microbiology, 2006, 152, 519-527, the genetic modification of *Mycoplasma genitalium* with different plasmids by electroporation is described, but no reference to Mhyo can be found.

The dissertation by B. Machado, *Construçao de vetor oriC de Mycoplasma hyopneumoniae—uma ferramenta para estudos genéticos do agente da Pneumonia Enzoótica Suína*, Porto Alegre, 2007, describes the transformation of the Mhyo strain 7448 with the replicative plasmid pOSTM by electroporation. To construct this plasmid, the oriC region of Mhyo and the expression cassette containing the tetracycline resistance gene (tetM), under the control of the *Spiroplasma citri* promoter gene, were introduced in the pUC18 vector. While the experimental part shows by means of PCR, the incorporation of the plasmid and the antibiotic resistance conferred by said vector, no conclusive results showing that the plasmid pOSTM was actually stably incorporated into Mhyo are provided in this work, since the isolation of the plasmids from the tetracycline-resistant transforming strains is not described. Furthermore, it is also described that the transforming strains had difficulties in growing after two passes in a selective medium. Consequently, these results show that using the transformation disclosed in this document it could not be possible to stably introduce an exogenous DNA sequence in a strain of Mhyo, since it cannot be recovered after multiple generations of the transformed bacteria.

Despite this disclosure in 2007, it has not been shown that the problem of the genetic modification of Mhyo was solved in subsequent studies.

In the report by M. Calcutt on the project entitled *Development of genetic manipulation protocols for Mycoplasma hyopneumoniae clade of animal pathogens*, University of Missouri, corresponding to the period Oct. 1, 2009 to Sep. 30, 2010 (downloaded from the web page http://www.reeis.usda.gov/web/crisprojectpages/220630.html, retrieved on Feb. 16, 2012), it is described that the objectives of the project is to develop methodology for the genetic manipulation of Mhyo. It is also described that it was intended to electrotransform Mhyo with plasmids including the tetracycline resistance gene. However, the results from the DNA analysis performed on the transforming bacteria were not positive and led the authors to consider that the transformation had not occurred. The results on the expression of this resistance gene were also not described.

The article by Browning et al., Developing attenuated vaccines to control mycoplasmoses, Microbiology Australia, 2011, 121-122, describes the development of vaccines containing temperature-sensitive strains of *Mycoplasma* that do not grow at the host's body temperature. Said strains were obtained by chemical mutation from wild type strains. The authors state that the directed genetic manipulation in Mhyo and *M. synoviae* continues to be a challenge and that it had not been achieved in said species. International patent application WO-A-2010/132932, from the same work group, also relates to temperature-sensitive strains of Mhyo.

In the article by Maboni et al., *Mycoplasma hyopneumoniae Transcription Unit Organization: Genome Survey and Prediction*, DNA Research, 2011, 18, 413-422, a comparative review of the genome of three strains of Mhyo (7448, J and 232) was conducted for the purpose of identifying open reading frames. The authors state that in spite of the development of the artificial transformation and other genetic tools for some species of *Mycoplasma*, these methodologies are yet to be developed for Mhyo.

Therefore, methods for the transformation of Mhyo have not been described in the state of the art, though there have been several unsuccessful attempts to perform such transformation.

Therefore, there is still a need to provide a method for preparing mutant strains of Mhyo by means of genetic engineering tools, thus providing mutant strains suitable for preparing vaccine compositions against porcine enzootic pneumonia and, eventually in combination with other antigen components, for the prevention and/or treatment of other porcine diseases.

DISCLOSURE OF THE INVENTION

The object of the present invention is a method for preparing mutant strains of Mhyo.

Another aspect of the invention is a replicative plasmid vector used in said method.

Another aspect of the invention is a transposon vector used in said method.

Another aspect of the invention is the use of said vector to prepare mutant strains of Mhyo.

Another aspect of the invention is a mutant strain of Mhyo obtainable by said method.

Another aspect of the invention is a mutant strain of Mhyo comprising an exogenous DNA sequence.

Another aspect of the invention is a mutant strain of Mhyo comprising the vector of the invention.

Another aspect of the invention is a strain of Mhyo transformed with the vector of the invention.

Another aspect of the invention is the use of said mutant strain as an expression host.

Another aspect of the invention is a vaccine comprising said mutant strain.

Another aspect of the invention is the use of the mutant strain of Mhyo of the invention for preparing a vaccine.

Another aspect of the invention is a vaccination kit comprising said mutant strain.

The authors of the present invention have developed a method for preparing mutant strains of Mhyo whereby exogenous DNA sequences can surprisingly be stably introduced into the cytoplasm or into the genome of a strain of Mhyo and the content of those sequences is expressed.

By the expression "an exogenous DNA sequence stably introduced into the cytoplasm or into the genome of a strain of Mhyo" it is understood that such sequence is not lost along the successive generations of the bacterium that has been transformed with said exogenous sequence. This stability means that the exogenous DNA sequence can replicate inside the transformed bacterium and in its descendants, and that it can be recovered after multiple generations of the transformed bacterium.

With the developed method, it is open a door to modifying strains of Mhyo for the first time by means of genetic engineering tools.

Mutant strains of Mhyo including exogenous DNA sequences can be prepared with said method. Said mutant strains can have different characteristics such as, for example, expressing a specific protein, or having a lower degree of virulence with respect to the wild type parental strain.

Said mutant strains can be used as vaccines, for example, live attenuated vaccines, inactivated vaccines, marker vaccines, which allow differentiating vaccinated animals from infected animals, or polyvalent vaccines against porcine enzootic pneumonia and another additional disease that can affect pigs, such as infections caused by porcine circovirus type 2 (PCV2), for example.

The process of the invention allowed for the first time to modify genetically Mhyo in stable form, and therewith it has been achieved, inter alia, the use of these transformed strains as expression vector of exogenous DNA sequences like, for example, nucleotide sequences coding for proteins of therapeutic or preventive interest such as the sequence of the PCV2 capsid, among others. By means of the technology disclosed in this invention, new vaccine candidates have been designed and prepared, which are also polyvalent, because they can be used to prevent different diseases by administering a single strain modified by means of the process of the invention.

In the present description and in the claims, the singular forms "a", "an" and "the" include plural references unless otherwise clearly indicated by the context.

Likewise, in the context of the invention the term "sequence" refers to a DNA sequence, except when it is explicitly indicated that it refers to an amino acid sequence.

The plasmid pOG contains the necessary elements so that this vector can replicate in Mhyo at the same time that allows the selection of the carrier cells of said plasmid. This plasmid has the oriC region of Mhyo (bases 2096 to 4043) and the gentamicin resistance marker gene (aac, bases 1 to 1816) under the control of the promoter of the gene of the Mhyo P97 protein (pp97, bases 1823 to 2087).

The plasmid pOGCRE derives directly from plasmid pOG and furthermore contains the cre gene of the phage P1 (bases 1 to 1032) under the control of the promoter pp97 (bases 1039-1303).

Unlike the previous plasmids, plasmid pOGA159 contains the tetracycline resistance gene (tetM, bases 945 to 2883) under the control of the promoter pp97 (bases 674-938). The oriC region of Mhyo is located between bases 2901-4848. Finally, it contains a segment of the Mhyo genome corresponding to the 5' end of the tlyA gene (a159, bases 4855 to 4980) reversely oriented and under the control of the promoter pp97 (bases 4996-5260).

Figure 2:
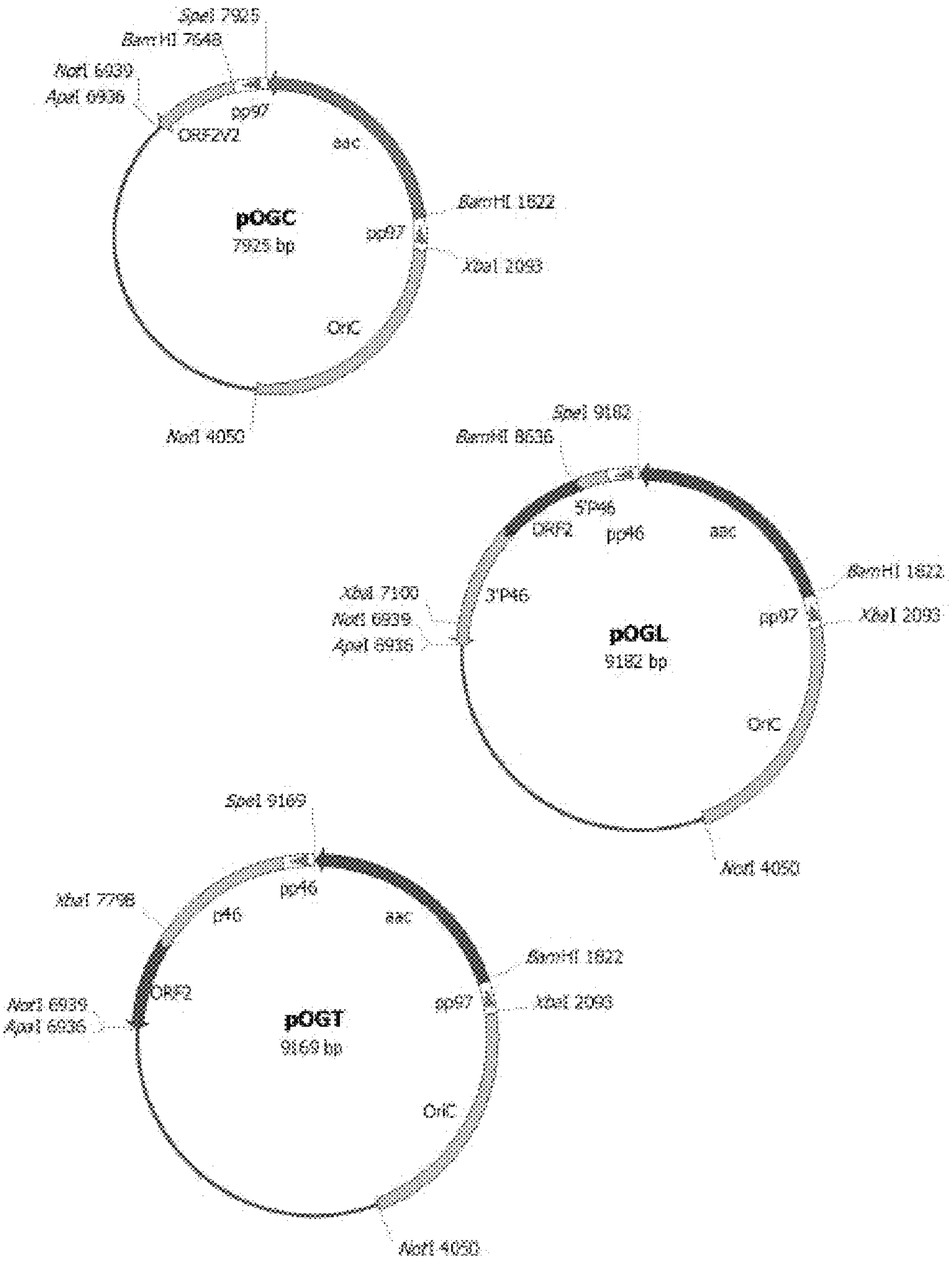

FIG. 2 shows a diagram of the replicative plasmids used to genetically modify Mhyo and to achieve the production of different recombinant versions of the protein of the PCV2 virus capsid. The promoters, the genes and the restriction enzyme sites used for cloning operations are indicated by arrows.

The plasmid pOGC contains exactly the same elements as the plasmid pOG (FIG. 1) and furthermore includes an additional copy of the promoter pp97 (bases 7654-7918) controlling the expression of the synthetic gene coding for the circovirus capsid included in the ORF2V2 (bases 6946-7647) of the PCV2 virus capsid. This plasmid allows the expression of the PCV2 capsid protein in the cytoplasm of the carrier cell.

The plasmid pOGL contains exactly the same elements as the plasmid pOG (FIG. 1) and furthermore includes the promoter sequence of the Mhyo P46 protein gene (pp46: bases 8918-9181) controlling the expression of a fusion of the gene of the protein of the PCV2 virus capsid (ORF2) inside of the gene coding for the P46 Mhyo membrane protein (bases 8642-8917 and 6946-7930). This plasmid produces a hybrid protein which is characterized in that amino acids 1 to 92 are from the N-terminal end of the P46 protein, amino acids 95 to 327 correspond to the protein of the PCV2 virus capsid and amino acids 330-656 are from the C-terminal end of the Mhyo P46 protein.

The plasmid pOGT contains exactly the same elements as the plasmid pOG (FIG. 1) and furthermore includes the promoter sequence pp46 (bases 8905-9169) controlling the expression of a fusion of the gene of the protein of the PCV2 virus capsid (ORF2) at the 3' end of the gene coding for the P46 Mhyo membrane protein (bases 7648-8904). This plasmid produces a hybrid protein which is characterized in that amino acids 1 to 419 are from the P46 protein and amino acids 420 to 652 correspond to the protein of the PCV2 virus capsid, ORF2 version (bases 6946-7647).

Figure 3:
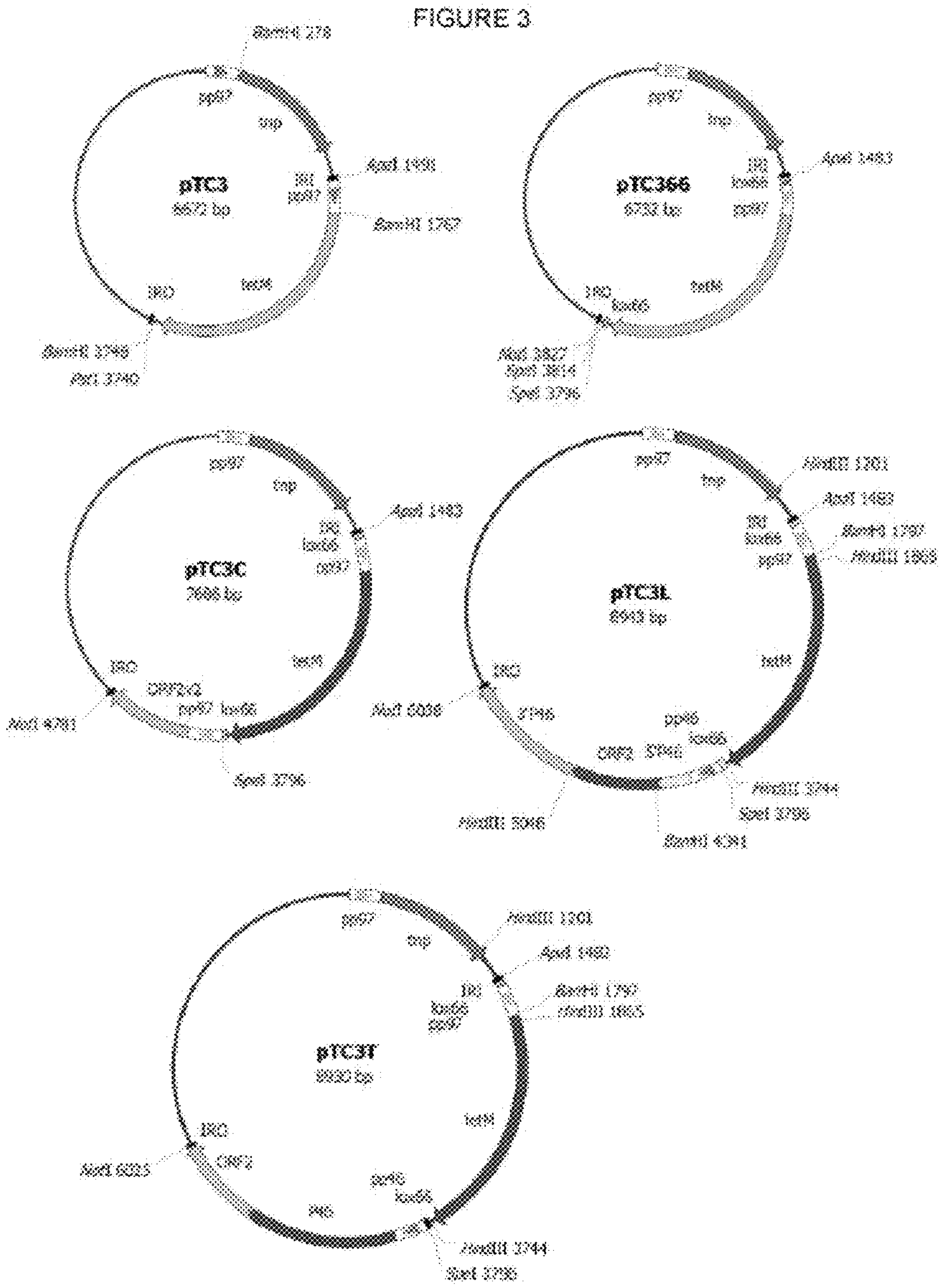

FIG. 3 shows a diagram of the plasmids carrying mini-transposons used to obtain insertions in the Mhyo chromosome. The promoters, genes and targets of restriction enzymes used for the construction of the plasmids and other important DNA sequences are indicated by arrows.

The plasmid pTC3 contains the elements necessary for obtaining strains of Mhyo bearing transposon insertions. This plasmid has been constructed on the backbone of the plasmid pMTn4001. The first element of this plasmid is the promoter pp97 (bases 7-271) controlling the expression of the transposase of plasmid pMTn4001 (bases 284-1261). Bases 1461-1486 and 3774-3799 correspond to the inverted repeats and are indicated in the diagram as IRI and IRO, respectively. The last element of this plasmid corresponds to the tetracycline resistance marker gene (bases 1761-3692), which is also under the control of the promoter of the Mhyo P97 protein (1502-1766).

Plasmid pTC366 derives directly from plasmid pTC3 and contains the lox66 sequences (substrate of the Cre recombinase, bases 1485-1518 and 3762-3795) flanking the tetracycline resistance marker gene TetM (bases 1791-3722).

Plasmid pTC3C derives directly from plasmid pTC366 and contains the gene coding for the protein of the PCV2 virus capsid ORF2V2 (bases 4078-4779) of the PCV2 virus, under the control of the promoter pp97 (bases 3808-4071). This plasmid promotes the synthesis of the recombinant protein corresponding to the PCV2 capsid protein in the cytoplasm of the strain of Mhyo transformed by said plasmid.

Plasmid pTC3L derives directly from plasmid pTC366 and contains a fusion of the gene of the protein of the PCV2 virus capsid (ORF2) inside of the gene coding for the P46 Mhyo membrane protein (bases 4347-5045 and 4066-4340 and 5052-6036, respectively), under the control of the promoter pp46 (bases 3801-4065). This plasmid promotes the synthesis of a hybrid protein, which is characterized in that amino acids 1 to 92 are from the N-terminal end of the P46 protein, amino acids 95 to 327 correspond to the protein of the PCV2 virus capsid and amino acids 330-656 are from the C-terminal end of the Mhyo P46 protein.

Plasmid pTC3T derives directly from plasmid pTC366 and contains a fusion between the gene of the protein of the PCV2 virus capsid (ORF2) and the gene coding for the P46 Mhyo membrane protein (bases 5322-6031 and 4065-5321, respectively), under the control of the promoter of the gene coding for the Mhyo P46 protein (bases 3801-4065). This plasmid promotes the synthesis of a hybrid protein which is characterized in that amino acids 1 to 419 are from the P46 protein and amino acids 420 to 652 correspond to the protein of the PCV2 virus capsid.

Figure 4:
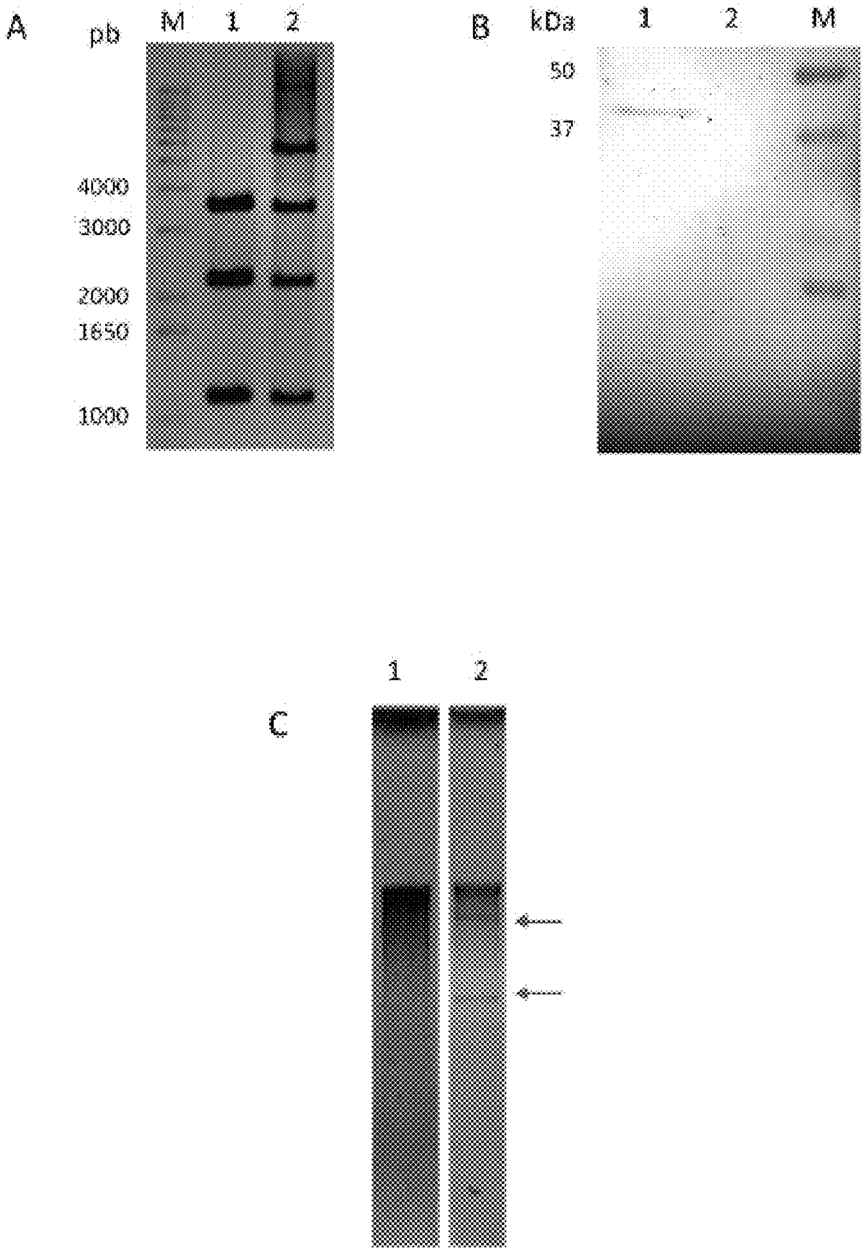

FIG. 4 shows the stability of the replicative plasmids and their use in the production of recombinant proteins.

This figure is split into 3 panels. Panel A shows a 0.7% agarose gel electrophoresis run at a voltage of 6V/cm for 2 hours. The 1 kb plus ladder molecular weight marker (Invitrogen) is in lane M. The plasmid pOG isolated from *E. coli* XI1-blue and digested with restriction enzyme ScaI is in lane 1. A total DNA extraction of the Mhyo strain 232POGc9 digested with restriction enzyme ScaI is in lane 2. The expected bands of the plasmid pOG digested with restriction enzyme ScaI are 3564 bp, 2225 bp and 1143 bp (FIG. 4, Panel A). By means of the comparison with the molecular weight marker and the bands of the plasmid isolated from *E. coli* XI1-blue, it is confirmed that the plasmid pOG propagates stably in the strain 232POGc9. The lengths of the different relevant DNA marker fragments are indicated on the left side of the figure.

Panel B shows a Western blot of a denaturing polyacrylamide gel electrophoresis with protein samples of different strains of Mhyo detected by means of a specific polyclonal antibody of the Cre recombinase of the bacteriophage P1. Lane 1 shows a protein extract of strain 232POGCREc1 where the expected band of 39 kDa is observed. Lane 2 shows an extract of the strain 232 where no bands are observed and the Precision Plus Protein Dual Xtra (Biorad) molecular weight marker is in lane M. The relevant molecular weights are shown in kDa on the right side of the figure. These results indicate that the plasmid pOGCRE is capable of producing the Cre protein once it is transformed into Mhyo strain 232.

Panel C shows an agarose gel electrophoresis in which DNA samples of Mhyo parental strain 6314 (lane 1) and of strain 6314pOGAc4, which is a product of the transformation of strain 6314 with the plasmid pOGA159 (lane 2), are analyzed. The arrows indicate the position of the two conformations adopted by plasmid pOGA159 in the transformed mutant strain of Mhyo.

Figure 5:
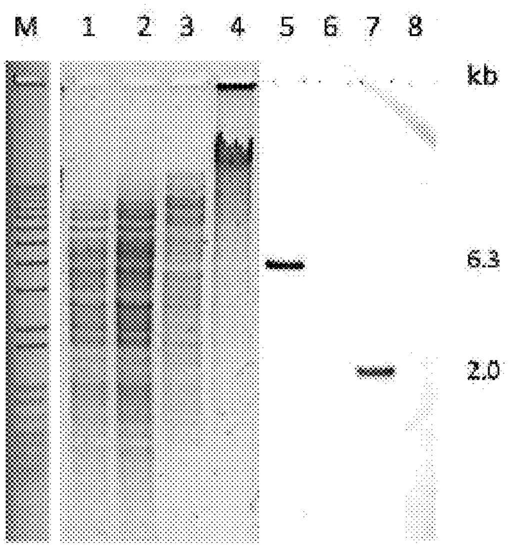
Figure 5:
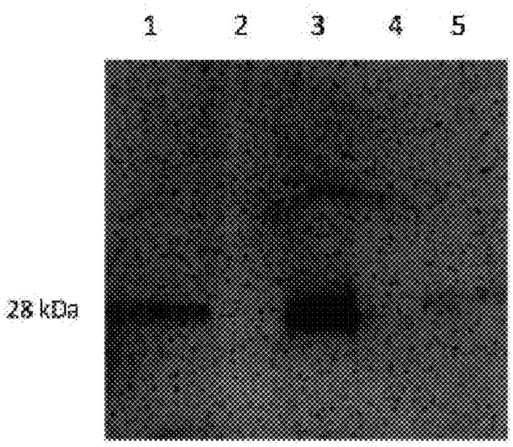

FIG. 5 shows the recovery of Mhyo strains bearing transposon insertions and the usefulness thereof in the production of recombinant proteins.

This figure is split into 3 panels. Panel A (lanes M and 1 to 4) shows a 0.7% agarose gel electrophoresis run at a voltage of 6V/cm for 2 hours whereas the right side of panel A (lanes 5 to 8) shows a Southern blot of this gel on a nylon membrane. The bands observed in the Southern blot correspond to the bands recognized by a probe designed against the TetM sequence under the control of the promoter of the Mhyo P97 protein. The 1 kb Plus Ladder (Invitrogen) molecular weight marker is in lane M. Lanes 1 and 5 correspond to a total DNA extraction from strain 232TC3hlyC digested with restriction enzyme EcoRI. Lanes 2 and 6 correspond to a total DNA extraction from strain 232 digested with restriction enzyme EcoRI. Lanes 3 and 7 correspond to a total DNA extraction of strain 232TC3hlyC digested with restriction enzyme EcoRV. Lanes 4 and 8 correspond to a total DNA extraction of strain 232 digested with EcoRV. The band of 6.3 kb in lane 5 and the band of 2 kb in lane 7 demonstrate the presence of the transposon containing the TetM resistance under the promoter of the P97 protein in the Mhyo genome whereas the absence of these bands in lanes 6 and 8 corroborate these results.

Panel B shows the results of an ELISA assay performed with the INGEZIM PCV DAS kit (Ingenasa, Spain) with different protein samples from Mhyo. The dilution used in each of the assays is indicated in the left column of the table, whereas the strain analyzed is shown in the upper row. The numerical results are the values from absorbance readings at 450 nm wavelength normalized by the amount of protein introduced in each well. All the strains of Mhyo transformed with the pTC3C, pTC3L and pTC3T vectors exhibit an absorbance that is clearly higher than that of the negative control, which indicates that the expression of the recombinant PCV2 capsid protein takes place in each one of these strains.

The panel C shows a Western blot of a denaturing polyacrylamide gel electrophoresis with protein samples of different strains of Mhyo detected by means of a specific monoclonal antibody of the PCV2 capsid protein. Lane 1 contains a protein extract of strain 232Cc6 where the expected band of 28 kDa is observed. Lane 2 contains a protein extract of strain 232 where no bands are observed. Lane 3 contains a protein sample of the PCV2 capsid supplied as a positive control in the INGEZIM PCV DAS kit (Ingenasa, Spain) where the expected band of 28 kDa is observed. Lane 4 contains a protein extract of strain 6314 where no bands are observed, whereas the protein extract of strain 6314Cc1 is in lane 5 where the expected band of 28 kDa is observed, though this band has a weaker intensity than those of lanes 1 and 3. These results indicate that in both 6314 and 232 strains the insertion in the Mhyo genome of the transposon present in the plasmid pTC3C induces expression of the PCV2 capsid protein, coded by ORF2v2.

Figure 6:
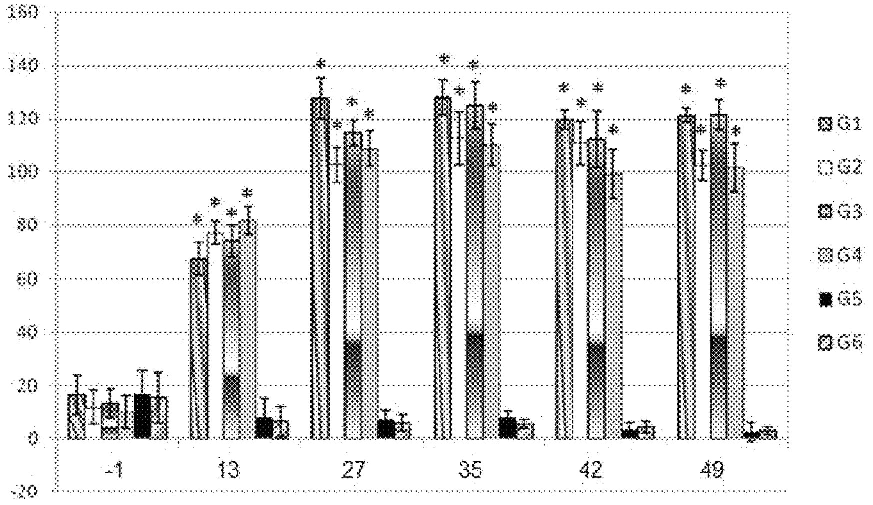

FIG. 6 shows the serological response to Mhyo obtained with the experimental vaccines, groups 1 to 4 of the Example 7.1. Groups 5 and 6 correspond respectively to the non-vaccinated, but infected control group and to the non-vaccinated and non-infected control group.

The day of the study when the analysis was performed is on the x-axis, and the S/P ratio (sample/positive) expressed as the % measured by ELISA is represented on the y-axis as an indicator of the IgG antibody response against Mhyo.

The asterisk indicates that the difference in relation to the non-vaccinated, but infected control group is statistically significant ($p<0.05$, according to the Mann-Whitney U test).

Figure 7:
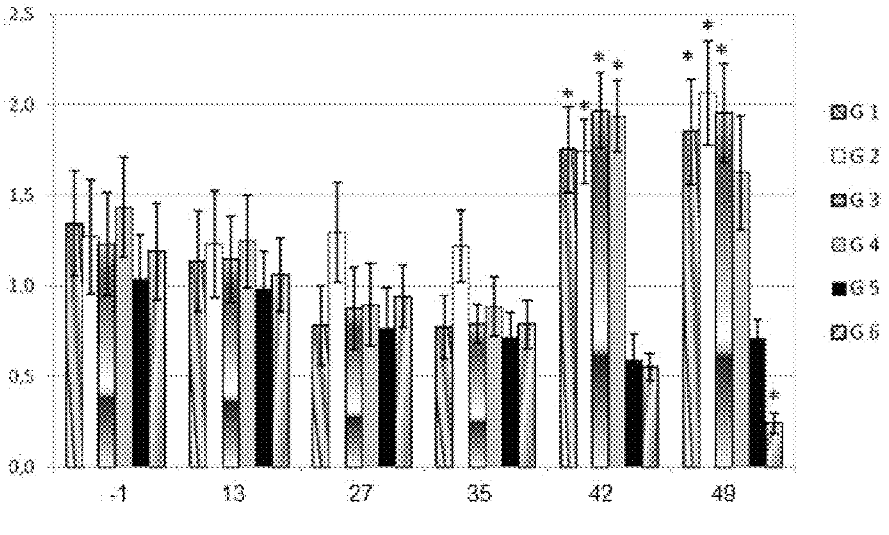

FIG. 7 shows the serological response to porcine circovirus (PCV2) obtained with the experimental vaccines, groups 1 to 4 of Example 7.1. Groups 5 and 6 correspond respectively to the non-vaccinated, but infected control group and to the non-vaccinated and non-infected control group.

The day of the study when the analysis was performed is on the x-axis, and the S/P ratio (sample/positive) expressed as the % measured by ELISA is represented on the y-axis as an indicator of the IgG antibody response against PCV2.

The asterisk indicates that the difference in relation to the non-vaccinated but infected control group is statistically significant ($p<0.05$, according to the one-way ANOVA test).

Figure 8:
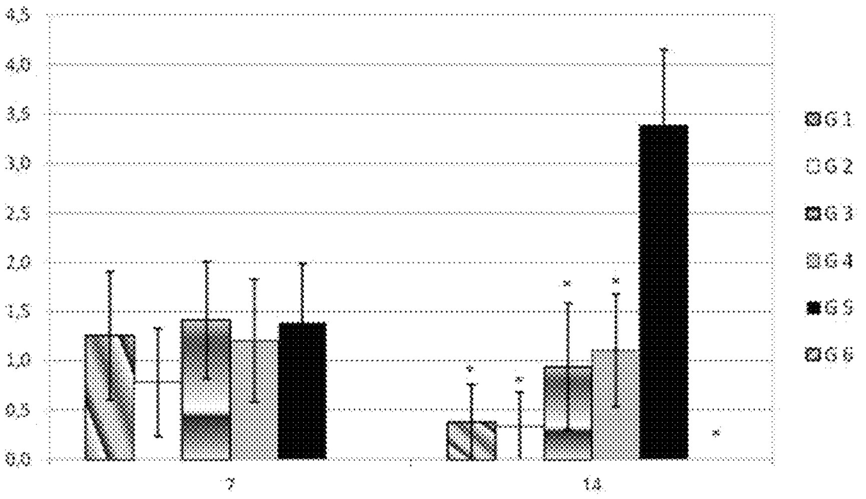

FIG. 8 shows the serum viral load in treatment groups 1 to 4, and in the control groups 5 and 6 of Example 7.1.

The day of the study when the analysis was performed is on the x-axis, and the $\log_{10}$ of the serum viral load of porcine circovirus type 2 (PCV2) expressed in copies/ml is represented on the y-axis.

The asterisk indicates that the difference in relation to the control group (non-vaccinated and infected) is statistically significant ($p<0.05$, according to the Mann-Whitney U test).

Figure 9:
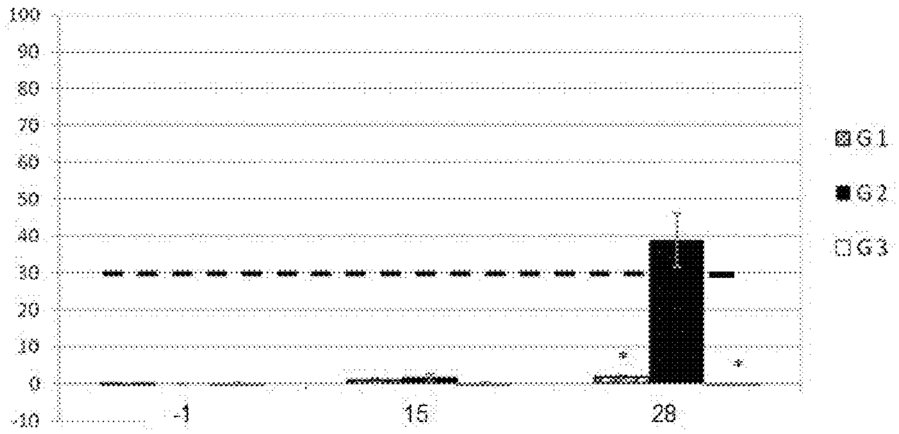

FIG. 9 shows the serological response to infection by Mhyo according to Example 8.2. Group 1 corresponds to the animals infected with the mutant strain of Example 4.8, group 2 corresponds to the animals infected with the wild type parental strain, and group 3 is the non-infected control group.

The day of the study when the analysis was performed is on the x-axis, and the S/P ratio (sample/positive) expressed as the % measured by ELISA is represented on the y-axis, as an indicator of the IgG antibody response against Mhyo.

The asterisk indicates that the difference in relation to the group infected with the wild type parental strain is statistically significant ($p<0.05$, according to the one-way ANOVA test).

Figure 10:
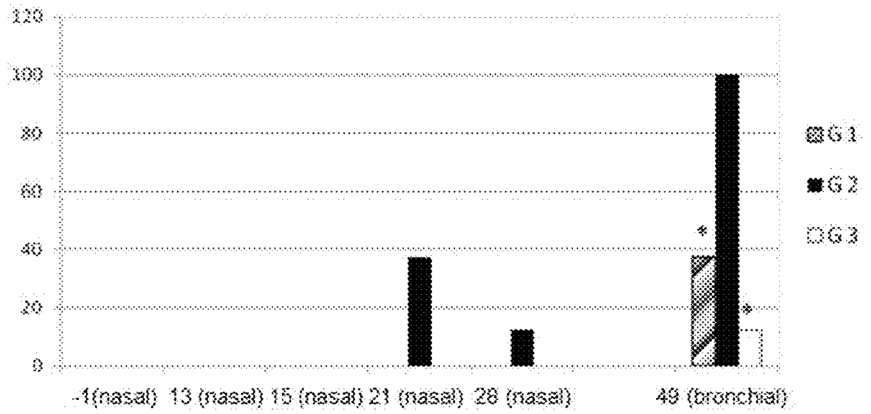

FIG. 10 shows the percentage of Mhyo PCR-positive animals of Example 8.2. Group 1 corresponds to the animals infected with the mutant strain of Example 4.8, group 2 corresponds to the animals infected with the wild type parental strain, and group 3 is the non-infected control group.

The day of the study when the analysis was performed is on the x-axis as is the type of sample analyzed (nasal or bronchial), and the percentage of PCR-positive animals is represented on the y-axis.

The asterisk indicates that the difference in relation to the group infected with the wild type parental strain is statistically significant ($p<0.05$, according to Fisher's exact test).

Figure 11:
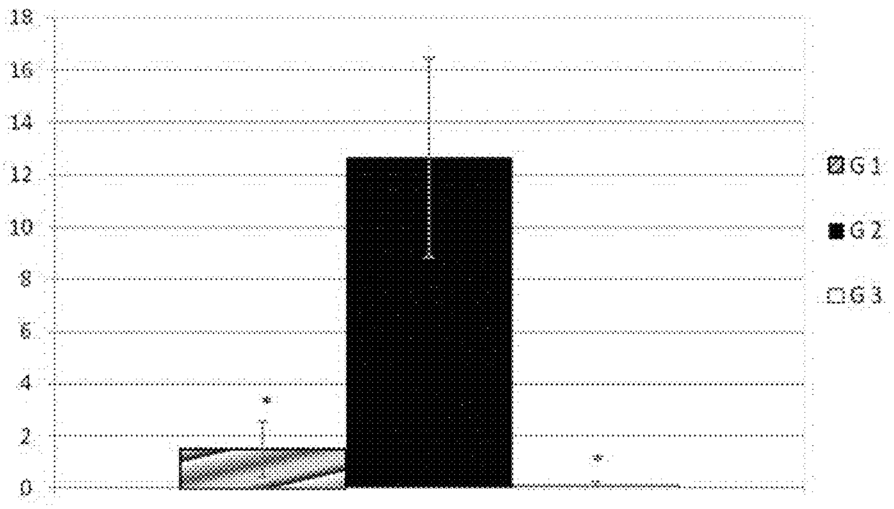

FIG. 11 shows the mean surface of lung affected by lesions which can be attributed to infection by Mhyo according to the assay of Example 8.2. Group 1 corresponds to the animals infected with the mutant strain of Example 4.8, group 2 corresponds to the animals infected with the wild type parental strain, and group 3 is the non-infected control group.

The mean value of the affected lung surface is represented on the y-axis.

The asterisk indicates that the difference in relation to the group infected with the wild type parental strain is statistically significant ($p<0.05$, according to the Mann-Whitney U test).

Figure 12:
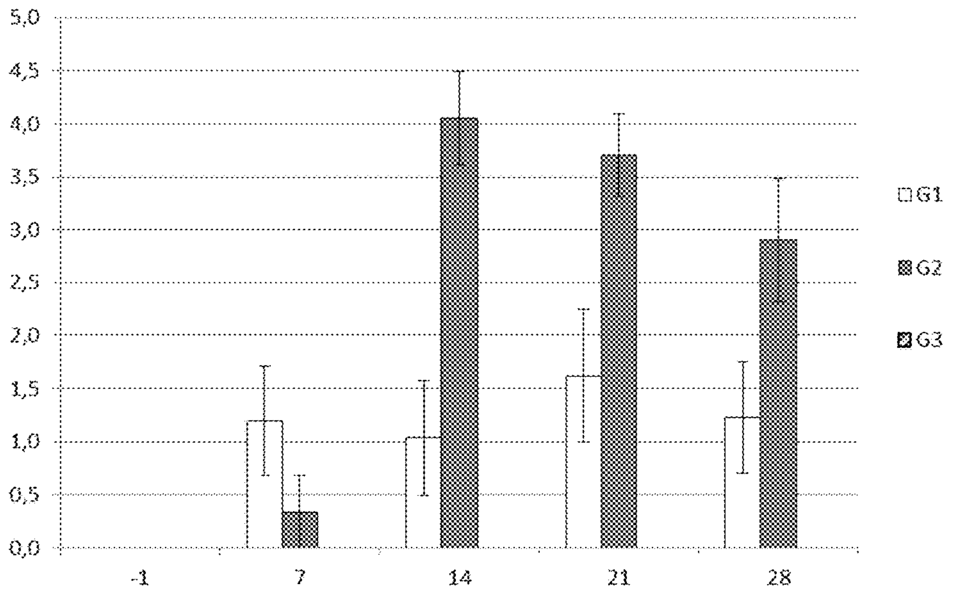

FIG. 12 shows the serum viral load determined in the treatment group 1, and in the control groups 2 and 3 of Example 7.2.

The day post-infection when the analysis was performed is on the x-axis, and the $\log_{10}$ of the serum viral load of porcine circovirus type 2 (PCV2) expressed in copies/ml determined by quantitative PCR is represented on the y-axis.

Figure 13:
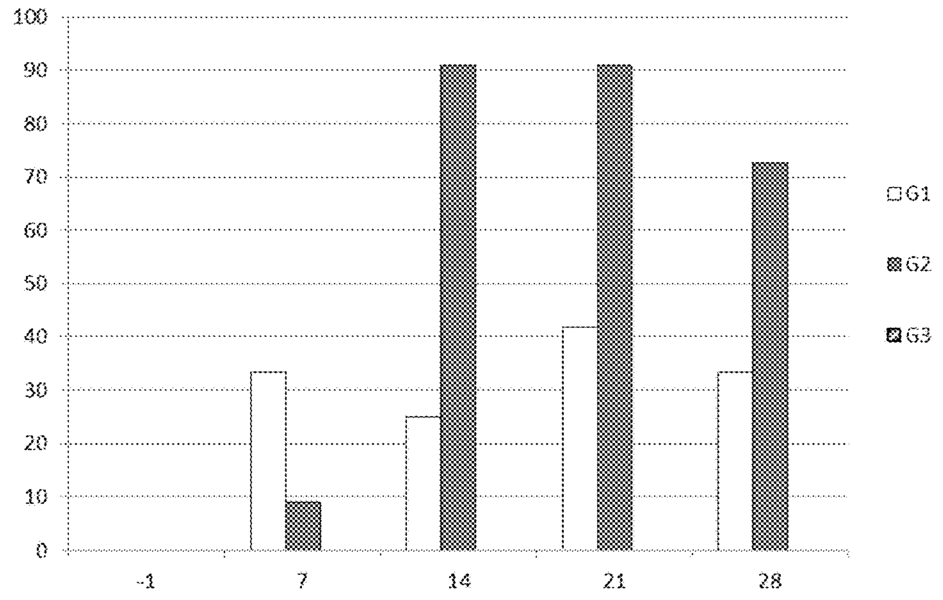

FIG. 13 shows the percentage of animals showing viremia by PCV2 in the treatment group 1, and in the control groups 2 and 3 of Example 7.2.

The day post-infection when the analysis was performed is on the x-axis, and the percentage of positive animals is represented on the y-axis.

Figure 14:
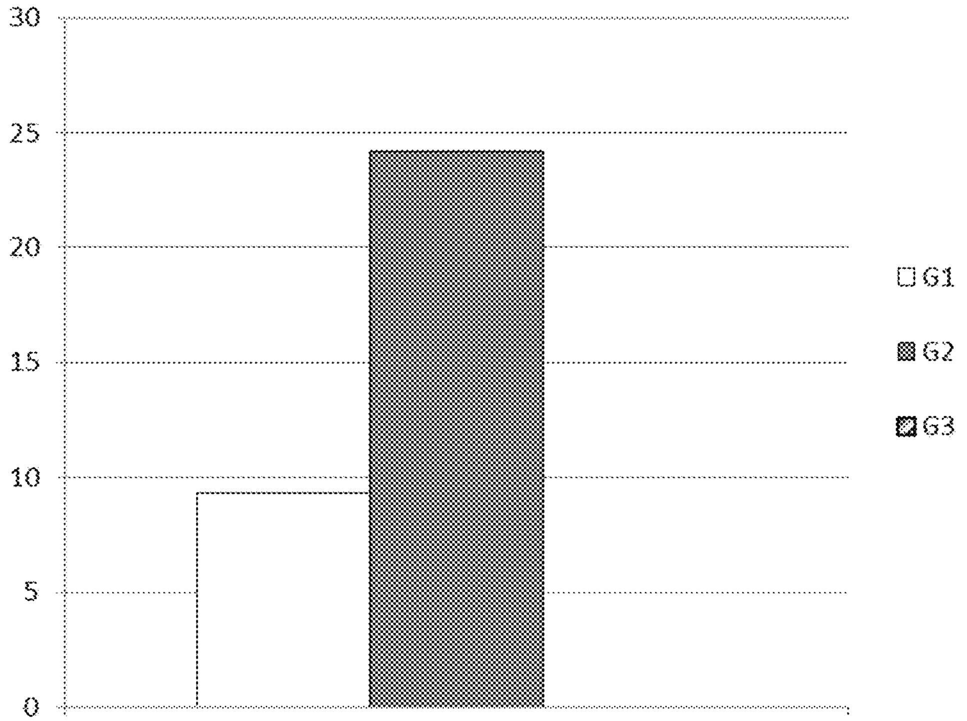

FIG. 14 shows the median surface of affected lung by Mhyo-like lesions expressed in percentage for the treatment group 1, and for the control groups 2 and 3 of Example 7.2 at the day 28 post-infection.

The group is on the x-axis, and the median surface of affected lung by Mhyo-like lesions is on the y-axis.

DETAILED DESCRIPTION OF THE INVENTION

The object of the invention is a method for preparing a mutant strain of *Mycoplasma hyopneumoniae* comprising the step of transforming a strain of *M. hyopneumoniae* by means of using a carrier vector comprising at least one exogenous DNA sequence, being that sequence under the control of a DNA sequence having a degree of identity of at least 80% with a promoter region of *M. hyopneumoniae.*

A mutant strain of Mhyo, stably incorporating an exogenous DNA sequence in the cytosol or in the genome thereof and expressing the content of said sequence, can be obtained by the method of the invention.

The method of the invention additionally comprises steps that are typical in methods for preparing mutant strains of bacteria, which are well known by the person skilled in the art and that are not essential for said method.

The method of the invention thus additionally comprises the steps of:

a) constructing a vector before transferring the vector to the bacterium in the transformation step, and
b) selecting the mutant bacteria that have been transformed with the exogenous DNA sequence after the transformation step.

The efficacy of the method of the invention is determined by means of isolating and characterizing the DNA sequences present in the transformed strains, as well as, for example, by means of checking for genotypic or phenotypic characteristics of the mutant strain or by means of checking the production of the recombinant proteins by the same, as it will be described below in the example section.

A mutant strain of Mhyo, stably incorporating an exogenous DNA sequence in the cytosol or in the genome thereof and expressing the content of said sequence, can be obtained by means of the carrier vector used in the method of the invention.

In a preferred embodiment the carrier vector is selected from the group formed by a replicative plasmid vector and a transposon vector.

In a preferred embodiment the carrier vector is a replicative plasmid vector. In the context of the invention "replicative plasmid vector" or "replicative plasmid" is understood as a vector carrying DNA sequences which replicates like an episomal element in the host bacterium, wherein an episomal element is a self-replicating extrachromosomal unit.

In the context of the invention, a replicative plasmid vector is that which allows to incorporate in a stable way an exogenous DNA sequence into the cytosol of a Mhyo bacterium and, optionally, to express an RNA or a protein coded by said sequence in the cytosol of the bacterium.

In a preferred embodiment the carrier vector is a vector, preferably a plasmid, wherein at least one exogenous DNA sequence comprised therein, is incorporated by transposition in the genome of the strain of Mhyo. This means that the strain is transformed by the carrier vector by transposition so that it is obtained a mutant strain of Mhyo incorporating by transposition in the genome a substantial part of the vector, which is that part comprised between the inverted repetitive sequences referred to as IRI and IRO, and which comprises at least one exogenous DNA sequence. Said inverted repetitions are the transposase target sequences.

In the context of the invention "transposon vector" is understood as a vector carrying DNA sequences wherein at least one of them is incorporated in the genome of the host by transposition.

In the method of the invention, a transposon vector is that, which allows to stably incorporate an exogenous DNA sequence in the genome of a bacterium of Mhyo.

Said incorporation takes places randomly in the genome of the bacterium. Therefore, depending on the specific site where said insertion occurs, any of the genes of the bacterium can be inactivated because their sequence is interrupted by the insertion of the transposon. If the inactivated gene is involved in Mhyo virulence factors, the resulting strain can be used to prepare an attenuated vaccine against PEP, and it further allows obtaining marker vaccines against PEP. Additionally, and like in the case of replicative vectors, the transposon can contain other genes under the control of a promoter region of Mhyo for expressing recombinant proteins with different functions.

As the genetic modification carried out by means of the method of the invention is integrated in the genome, the transformed strain is stable over the next generations.

Exogenous DNA Sequence

In the context of the invention, "exogenous DNA sequence" is understood as a DNA fragment that is stably introduced in the cytosol or in the genome of the strain of Mhyo.

It has been found that by means of the method of the invention an exogenous DNA sequence can be stably introduced in a strain of Mhyo because said sequence is not lost over successive generations of the bacterium that has been transformed with said exogenous sequence. This stability means that the exogenous DNA sequence can replicate inside the transformed bacterium and in its offspring and can be recovered after multiple generations of the transformed bacterium.

The exogenous DNA sequence can be quite diverse and has a broad definition, as explained below.

In the context of the invention, said sequence can be, for example, a marker gene. The vector comprising the exogenous DNA sequence usually comprises said marker to be able to easily select the mutant strains that have been transformed. Said genetic marker can be, for example, an antibiotic resistance gene. These may include, for example, the TetM gene, which confers resistance to the tetracycline from the plasmid pIVT-1, described in Dybvig et al., J. Bacteriol, 2000, 182, 4343-4347, or the aac(6')-aph(2") gene, which confers resistance to aminoglycoside antibiotics, such as gentamicin, for example, and which is described in Chow et al., Antimicrob. Agents Chemother., 2001, 45/10), 2691-2694. The gene for phenotypic selection is preferably the TetM gene.

The exogenous DNA sequence can also be a gene coding for recombinant proteins such as, for example, the Cre recombinase of bacteriophage P1, or the transposase of transposon Tn4001, or transposase target sequences such as, for example, IRI or IRO.

The exogenous DNA sequence can also be a gene coding for a recombinant protein of therapeutic or preventive interest. Said protein can be related to virulence factors or antigenic determinants of microorganisms causing diseases in pigs, and is capable of inducing or contributing to the induction of a protective response against diseases or pathological conditions that may affect pigs. The exogenous DNA sequence preferably codes for a recombinant protein that induces a protective response against diseases or pathological conditions affecting pigs caused by the microorganisms of the group formed by *Actinobacillus* sp., *Brachyspira* sp., *Pasteurella multocida, Salmonella* sp., *Streptococcus* sp., *Isospora* sp., *Erysipelothrix rhusiopathiae, Leptospira* sp., *Staphylococcus* sp., *Haemophilus parasuis, Bordetella bronchiseptica, Clostridium* sp., *Mycoplasma* sp., *Lawsonia intracellularis, Escherichia coli*, porcine reproductive and respiratory syndrome virus, swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV) and porcine circovirus. Among them, for example, the gene coding for the glycoprotein 5 (gp5) of the porcine reproductive and respiratory virus (PRRS), the gene coding for the capsid protein of the porcine circovirus type 2 (PCV2), the gene coding for the glycoprotein E (gpE) of the classical swine fever virus, the gene coding for the sp1 protein of the porcine parvovirus (PPV), the gene coding for the toxin of *Pasteurella multocida*, the gene coding for the dermonecrotoxin of *Bordetella bronchiseptica*, the genes coding for the toxins of *Clostridium* spp, *Escherichia coli*, or *Actinobacillus pleuropneumoniae*. In a preferred embodiment, said protein induces a protective response against the mentioned diseases.

A DNA fragment from Mhyo, optionally reordered or recombined with other DNA fragments, is also considered as an exogenous DNA sequence. Examples of this exogenous DNA sequence are, for example, the origin of replication oriC of Mhyo, an antisense RNA sequence, or the gene coding for the Mhyo P97 or P46 protein, to increase the transcription and translation rate of said gene.

The exogenous DNA sequence is preferably selected from the group comprising an antibiotic resistance gene, a gene coding for a recombinase, a gene coding for a transposase, a transposase target sequence, a DNA fragment from Mhyo, fragment which preferably has been reordered or recombined with one or several DNA fragments, a gene coding for an antigenic component of a microorganism causing porcine diseases, and combinations thereof; more preferably it is a marker gene which confers resistance to an antibiotic, a gene coding for an antigenic component of a microorganism causing porcine diseases, or combinations thereof; and even more preferably it is an antibiotic resistance gene combined with a gene coding for an antigenic component of a microorganism causing porcine diseases, preferably a gene coding for the capsid protein of the porcine circovirus type 2 (PCV2), and optionally combined with a gene coding for a Mhyo membrane protein, preferably the Mhyo P46 protein.

Promoter Region of Mhyo

In the context of the invention, "promoter region of Mhyo" is understood as a DNA sequence characteristic of Mhyo which initiates or promotes the transcription of a Mhyo DNA sequence.

The DNA sequence which initiates or promotes the transcription of the exogenous DNA sequence has a degree of identity of at least 80%, preferably of at least 85%, more preferably of at least 90%, even more preferably of at least 95%, more preferably of at least 99%, and even more preferably 100% with a promoter region of Mhyo.

In a particularly preferred embodiment, the DNA sequence which initiates or promotes the transcription of the exogenous DNA sequence has a degree of identity of 100% with a promoter region of Mhyo.

A sequence, which induces the synthesis of a messenger RNA (transcript) towards its 3' end once identified by the RNA polymerase holoenzyme, is understood as promoter region. This transcript is normally translated and produces a protein with a specific function, or it leads to an RNA that intervenes in protein synthesis or in the regulation of said transcriptional activity.

The skilled person in the art knows the meaning of the expression "a promoter region" and it can be identified by standard means.

The promoter region of Mhyo corresponds to a DNA segment preferably comprising at least 50 base pairs, preferably at least 100 base pairs, more preferably at least 200 base pairs, and even more preferably between 200 and 300 base pairs, located on the 5' side of well-established Mhyo coding sequences.

In a particularly preferred embodiment, the DNA sequence used as the promoter in the method and in the carrier vector of the invention has a degree of identity of 100% with a promoter region of Mhyo, comprising at least 50 base pairs.

In an even more preferred embodiment, the DNA sequence used as the promoter in the method and in the carrier vector of the invention has a degree of identity of 100% with a promoter region of Mhyo, comprising between 200 and 300 base pairs.

In the context of the invention, "well established coding sequences" is understood as those DNA sequences coding for Mhyo proteins or transcriptionally active regions of the Mhyo genome which lead to, for example, an RNA that intervenes in protein synthesis or in the regulation of the transcriptional activity. These sequences include, for example, the P46, P65, P97, and P102 surface proteins, described in Minion et al., J. Bacteriol., 2004, 186(21), 7123-7133; the P76, P146, P216 adhesins or the P95 membrane protein, described in Vasconcelos et al., J. Bacteriol., 2005, 187(16), 5568-5577, or the P36 cytosolic protein described in Caron et al., J. Clin. Microbiol., 2000, 38(4), 1390-1396, or ribosomal RNA.

In a preferred embodiment, the promoter region of Mhyo comprises the promoter region of the gene of a Mhyo protein selected from the group formed by the P36, P46, P65, P76, P97, P102, P146, and P216 proteins, more preferably the P46 and P97 proteins, even more preferably it is selected from the group comprising the promoter region of the mhj_0194 gene of Mhyo strain J coding for the P97 protein and corresponding to the DNA sequence comprised between bases 214293 and 214557 of the Mhyo strain J (SEQ ID NO: 1), and the promoter region of the gene mhj_0511 of the Mhyo strain J (SEQ ID NO: 2), coding for the P46 protein and corresponding to the DNA sequence comprised between bases 656451 and 656713 of Mhyo strain J deposited in the GenBank database with number AE017243 and described in Vasconcelos et al., mentioned above.

The promoter region of Mhyo, which controls the exogenous sequences, can be the same for all sequences or can be different. Preferably it is the same.

A DNA promoter sequence can be easily identified by the person skilled in the art by selecting a DNA sequence having a degree of identity of at least 80%, more preferably of at least 90%, more preferably of at least 95%, even more preferably of at least 99%, and even more preferably of 100%, with a promoter region of Mhyo, preferably comprising at least 50 base pairs, preferably at least 100 base pairs, more preferably at least 200 base pairs, and even more preferably between 200 and 300 base pairs, located on the 5' side of well-established Mhyo coding sequences, and carrying out the method of the invention. The methods for identifying a DNA promoter sequence are described, for example, in the Sambrook and Russell manual, *Molecular Cloning* 3rd Ed. Cold Spring Harbor Laboratory Press, Cold Spring Harbor N.Y. (2001).

Replicative Plasmid Vector

An object of the invention is a replicative plasmid vector comprising:

1) a DNA sequence comprising the oriC region of a strain of *Mycoplasma* sp., and
2) an exogenous DNA sequence comprising a marker gene, and optionally an additional exogenous DNA sequence, which are under the control of a DNA sequence having a degree of identity of at least 80%, 90%, 95%, 99% or 100% with a promoter region of Mhyo.

In a particularly preferred embodiment, the DNA sequence, which initiates or promotes the transcription of the exogenous DNA sequence, comprises between 200 and 300 base pairs and has a degree of identity of 100% with a promoter region of Mhyo.

In the replicative plasmid of the invention, a promoter region of Mhyo, selected from the group comprising the promoter region of the gene of the Mhyo P97 protein, and the promoter region of the gene of the Mhyo P46 protein, is preferably used, the promoter region of Mhyo preferably comprises the promoter region of the gene of the Mhyo P97 protein, or alternatively the promoter region of the gene of the Mhyo P46 protein mentioned above.

The promoter region of Mhyo, which controls sequences comprised in the replicative plasmid, can be the same for all the sequences or it can be different. It is preferably the same sequence.

The oriC region allows the introduced DNA fragment to replicate like an episomal element and to stably maintain this DNA fragment in the offspring of the transformed cell, preferably maintaining the conditions for phenotypic selection.

In the replicative plasmid vector of the invention the oriC region is the oriC region of a strain of *Mycoplasma* sp.

In the context of the invention, *Mycoplasma* sp. is understood as any bacterium of the *Mycoplasma* genus, such as, for example, *M. pneumoniae, M. hyopneumoniae, M. hominis, M. genitalium, M. pulmonis, M. capricolum, M. mycoides, M. ovipneumoniae, M. haemofelis, M. gallisepticum, M. laboratorium*, or *M. bovis*, among others.

In a preferred embodiment, the oriC region belongs to a strain of Mhyo, more preferably it belongs to strain J, and more preferably it comprises the DNA sequence comprised between bases 897262 and 1802 of Mhyo strain J.

The marker gene, also referred to as gene for phenotypic selection, allows selecting the clones which have incorporated the plasmid with the exogenous DNA sequence, as explained above.

In a preferred embodiment, the vector comprises an additional exogenous DNA sequence. Mutant strains of Mhyo, which can be used to prepare monovalent or polyvalent vaccines, optionally marker vaccines, and they can also express useful genetic tools for the subsequent modification of said mutants such as, for example, the Cre recombinase of phage P1, the FLP recombinase of *Saccharomyces cerevisiae*, the tetracycline repressor protein (TetR), or they can completely or partially block the translation of a specific Mhyo gene, can be obtained by means of said additional exogenous DNA sequence.

The additional exogenous DNA sequences, which can be incorporated in the replicative plasmid, include, for example, the ORF cre gene coding for the Cre recombinase of phage P1.

Cre recombinase has the capacity to split DNA regions flanked by loxP type sequences. Thereby, for example, if the replicative plasmid includes the cre ORF gene, and a resistance gene to an antibiotic flanked by loxP type sequences, for example, lox66, when Cre recombinase is expressed the antibiotic resistance is eliminated by the transformed bacterium. In other words, in subsequent steps the marker gene can be removed. This is important in the case of preparing transformed mutant strains of Mhyo having an attenuated virulence and used for preparing live vaccines, in which the presence of a resistance gene to an antibiotic is an undesirable feature.

In a preferred embodiment, the replicative plasmid further comprises an additional exogenous DNA sequence coding for a recombinant protein of therapeutic or preventive interest. Said protein can be related to virulence factors or antigenic determinants of microorganisms causing diseases in pigs, and it is capable of inducing or contributing to the induction of a protective response against diseases or pathological conditions which may affect pigs caused by the microorganisms described above.

In a preferred embodiment, the replicative plasmid comprises at least twice the additional exogenous DNA sequence coding for a recombinant protein of therapeutic or preventive interest, preferably twice, and more preferably twice or three times. In this way several copies of the additional exogenous DNA sequence are introduced and the expression yield of that protein is increased. The promoter region of Mhyo which controls the sequences comprised in the replicative plasmid can be the same for all sequences or can be different.

In a still more preferred embodiment, the additional exogenous DNA sequence is selected from the group formed by the sequence coding for the capsid protein of porcine circovirus type 2 (PCV2) and the exogenous DNA sequence coding for a protein comprising the capsid protein of porcine circovirus type 2 (PCV2) additionally bearing MetSerGlySer (SEO ID NO: 46) amino acids at the N-terminal end of said protein, wherein said capsid protein is described in the GenBank database with the 15 accession number AAC61864 (SEQ ID NO: 6).

In an even more preferred embodiment, the additional exogenous DNA sequence codes for the PCV2 capsid protein using the most common codon in the Mhyo genome for each of the amino acids corresponding to said protein selected from the group formed by SEQ ID NO: 3, SEQ ID NO: 4, and SEQ ID NO: 5.

SEQ ID NO: 3 has 699 base pairs, SEQ ID NO: 4, has 702 base pairs, and SEQ ID NO: 5 has 992 base pairs, a DNA sequence with a length substantially greater than the other two because it also incorporates the promoter region of the gene of the P97 protein, corresponding to the DNA sequence comprised between bases 214293 and 214557 of the Mhyo strain J, to thus simplify the cloning steps. In this description SEQ ID NO: 5 is also referred to as ORF2v2.

In a preferred embodiment, the additional exogenous DNA sequence comprises the gene of the protein of the PCV2 virus capsid (ORF2) fused to the last base coding for the gene of a Mhyo membrane protein, preferably the Mhyo membrane protein is selected from the group consisting of the P46 protein and the P97 protein, more preferably it is the P46 protein, more preferably under the control of the promoter of the Mhyo P46 or P97 protein genes, and even more preferably under the promoter of the Mhyo P46 protein gene.

In the case of the P46 protein, the fusion takes place at the 3' end of the gene coding for said membrane protein (bases 7648-8904). This plasmid directs the synthesis of a hybrid protein which is characterized in that amino acids 1 to 419 are from the P46 protein and amino acids 420 to 652 correspond to the protein of the PCV2 virus capsid, ORF2 version (bases 6946-7647).

In a preferred embodiment the additional exogenous DNA sequence comprises the gene coding for the PCV2 capsid protein inserted in the DNA sequence coding for a loop of a Mhyo membrane protein, preferably the Mhyo membrane protein is selected from the group consisting of the P46 protein and the P97 protein, more preferably it is the P46 protein, more preferably under the control of the promoter of the Mhyo P46 or P97 protein genes, and even more preferably under the promoter of the Mhyo P46 protein gene.

In the case of the preferred embodiment with the P46 protein, the plasmid directs the synthesis of a hybrid protein which is characterized in that amino acids 1 to 92 are from the N-terminal end of the P46 protein, amino acids 95 to 327 correspond to the protein of the PCV2 virus capsid and amino acids 330-656 are from the C-terminal end of the Mhyo P46 protein.

Loops are identified in amino acid sequences by means of methods well known by the person skilled in the art, whereby it is possible to predict their location with reasonable effectiveness.

Said loops generally present high flexibility and have a good tolerance for the insertion of amino acid sequences from other proteins. Furthermore, since they are exposed on the surface of the bacteria, they enable the generation of a good immunogenic response.

In a preferred embodiment, the replicative plasmid comprises an additional exogenous DNA sequence which is a Mhyo gene reversely oriented with respect to the promoter region of Mhyo, preferably the Mhyo gene codes for a Mhyo virulence factor, preferably under the control of the promoter of the Mhyo P46 or P97 protein, and even more preferably under the promoter of the Mhyo P46 protein.

Said DNA sequence is capable of producing an antisense RNA, which can block the translation of said Mhyo gene. If it is a gene coding for a Mhyo virulence factor, the transformation may reduce the degree of virulence of the microorganism.

In a more preferred embodiment, the replicative plasmid comprises the sequence comprised between bases 194,535 and 194,654 of the genome of Mhyo strain J reversely oriented with respect to the promoter region of Mhyo.

Said sequence produces an antisense RNA which can block the translation of the tlyA gene of said strain, which corresponds to a Mhyo hemolysin.

The Examples describe the preparation of plasmids pOG, pOGCRE, pOGA159, pOGC, pOGL and pOGT. The first incorporates the aac(6')-aph(2") gene which confers gentamicin resistance. Furthermore plasmid pOGCRE incorporates the ORF cre gene, coding for the Cre recombinase of phage P1; plasmid pOGA159 incorporates an inhibitory sequence of the translation of the hemolysin a159 gene of Mhyo; whereas plasmids pOGC, pOGL and pOGT incorporate furthermore genes coding for different protein versions of the capsid protein of porcine circovirus type 2 (PCV2).

Transposon Vectors

Another object of the invention is a transposon vector, preferably a plasmid, comprising:

1) a DNA sequence coding for a transposase,
2) an exogenous DNA sequence comprising a marker gene and,
3) optionally, an additional exogenous DNA sequence, wherein the DNA sequence coding for a transposase and at least one of the exogenous DNA sequences are under the control of a DNA sequence having a degree of identity of at least 80%, 85%, 90%, 95%, 99% or 100% with a promoter region of Mhyo.

In a particularly preferred embodiment, the DNA sequence, which initiates or promotes the transcription of the DNA sequences, comprises between 200 and 300 base pairs and has a degree of identity of 100% with a promoter region of Mhyo.

The gene coding for a transposase contains a DNA sequence coding for an enzyme, which binds to a specific sequence in the transposon and catalyzes the movement of said transposon to another part of the genome. The selection of the gene coding for a transposase is not critical. Genes coding for a transposase include transposon TN4001 T incorporated in plasmid pIVT-1, mentioned above, or transposon Tn916 incorporated in plasmid pAM120, described in, for example, Cao et al., J. Bacteriol., 1994, 176(14), 4459-4462.

The marker gene or gene for phenotypic selection can be a resistance gene to an antibiotic, such as, for example, the TetM gene or the aac(6')-aph(2") gene, mentioned above. The gene for phenotypic selection is preferably the TetM gene.

The marker gene is flanked by two inverted repeats, such as those of the transposon present in the plasmid pIVT-1, mentioned above. Said sequences are recognized by the transposase, and without them the gene for phenotypic selection would not be able to move to the bacterial chromosome and the genetic modification would not be carried out. As the genetic modification is integrated in the genome, it will be stably maintained over the following generations of the transformed cell.

The inverted repeats preferably present the sequences SEQ ID NO: 7 for IRO and SEQ ID NO: 8 for IRI.

A promoter region of Mhyo selected from the group comprising the promoter region of the gene of the Mhyo P97 protein, and the promoter region of the gene of the Mhyo P46 protein, as described above, is preferably used in the transposon vector of the invention. The promoter region of Mhyo preferably comprises the promoter region of the gene of the Mhyo P97 protein, or alternatively the promoter region of the gene of the Mhyo P46 protein.

The promoter region of Mhyo, which controls the sequences comprised in the transposon vector, can be the same for all sequences or can be different. Preferably it is the same.

Similar to that explained in the case of a replicative plasmid, in a preferred embodiment, the transposon vector further comprises an additional exogenous DNA sequence coding for a recombinant protein of interest. Said protein is capable of inducing or contributing to the induction of a protective response against diseases or pathological conditions which may affect pigs.

In a preferred embodiment, the transposon vector comprises at least twice the additional exogenous DNA sequence coding for a recombinant protein of therapeutic or preventive interest, preferably twice, and more preferably twice or three times. In this way several copies of the additional exogenous DNA sequence are introduced and the expression yield of that protein is increased. The promoter region of Mhyo, which controls the sequences comprised in the transposon vector, can be the same for all sequences or can be different.

In a still more preferred embodiment, the additional exogenous DNA sequence is selected from the sequence coding for the capsid protein of the porcine circovirus (PCV2) and an exogenous DNA sequence coding for a protein comprising the capsid protein of the porcine circovirus (PCV2), additionally bearing MetSerGlySer amino acids at the N-terminal end of said protein, wherein the capsid protein of the porcine circovirus (PCV2) is described in the GenBank database with the accession number AAC61864 (SEQ ID NO: 6).

In an even more preferred embodiment, the additional exogenous DNA sequence codes for the PCV2 capsid protein using the most common codon in the Mhyo genome for each of the amino acids corresponding to said protein selected from the group formed by SEQ ID NO: 3, SEQ ID NO: 4, and SEQ ID NO: 5, wherein each of the DNA sequences is under the control of a promoter region of Mhyo. SEQ ID NO: 5, which already includes the promoter region of the gene coding for the Mhyo P97 protein is more preferably used.

In a preferred embodiment, the additional exogenous DNA sequence comprises the DNA sequence coding for the PCV2 capsid protein fused to the last base coding the gene of a Mhyo membrane protein, preferably the membrane protein is selected from the group consisting of the P46 protein and the P97 protein, more preferably it is the P46 protein. The strain transformed with this plasmid expresses the Mhyo protein in which the amino acids corresponding to the PCV2 capsid protein are located immediately after its last amino acid, i.e., it expresses a hybrid protein formed by the Mhyo P46 or P97 protein and the PCV2 capsid protein. Taking into account that it is a membrane protein, the strain of Mhyo transformed with said plasmid expresses the fusion of both proteins in the bacterium membrane. The PCV2 capsid protein is selected from the group formed by SEQ ID NO: 3, SEQ ID NO: 4, and SEQ ID NO: 5, more preferably it is SEQ ID NO: 4. The promoter region of Mhyo is preferably the promoter region of the gene coding for the Mhyo P97 or P46 protein, and even more preferably the promoter of the Mhyo P46 protein.

In another preferred embodiment, the additional DNA sequence comprises the gene coding for the PCV2 capsid protein inserted into the DNA sequence coding for a loop of a Mhyo membrane protein, the membrane protein is preferably selected from the group consisting of the P46 protein and the P97 protein, more preferably it is the P46 protein. The strain transformed with this plasmid expresses the PCV2 capsid protein inserted between the Mhyo P46 or P97 protein, i.e., it expresses a hybrid protein formed by the Mhyo P46 or P97 protein and the PCV2 capsid protein. The PCV2 capsid protein is selected from the group formed by SEQ ID NO: 3, SEQ ID NO: 4, and SEQ ID NO: 5, more preferably it is SEQ ID NO: 3.

In a preferred embodiment, the PCV2 capsid protein is inserted between amino acids 92 and 93 of the P46 protein.

The following transposon vectors, preferably plasmids, are especially preferred:

1) Vector comprising the DNA sequence coding for a transposase, preferably transposon TN4001T, a DNA sequence coding for a marker gene, preferably the tetM gene, optionally flanked by loxP type sequences, and a DNA sequence coding for the PCV2 capsid protein, preferably defined by SEQ ID NO: 5, wherein each of the DNA sequences is under the control of a promoter region of Mhyo selected between the promoter region of the Mhyo P97 protein or P46 protein, preferably the promoter region of the P97 protein. An example of this type of plasmid is that is referred to as pTC3C and described in the Example section.
2) Vector comprising the DNA sequence coding for a transposase, preferably transposon TN4001T, a DNA sequence coding for a marker gene, preferably the tetM gene, optionally flanked by loxP sequences, and a DNA sequence coding for the PCV2 capsid protein, preferably defined by SEQ ID NO: 4, which is fused to the last base coding the gene of a Mhyo membrane protein, preferably the membrane protein is selected from the group consisting of the P46 protein and the P97 protein, more preferably it is the P46 protein, wherein each of the DNA sequences is under the control of a promoter region of Mhyo selected between the promoter region of the Mhyo P97 or P46 protein, preferably the promoter region of the P46 protein. An example of this type of plasmid is that referred to as pTC3T and described in the Example section.
3) Vector comprising the DNA sequence coding for a transposase, preferably transposon TN4001T, a DNA sequence coding for a marker gene, preferably the tetM gene, optionally flanked by loxP type sequences, and a DNA sequence coding for the PCV2 capsid protein, preferably defined by SEQ ID NO: 3, which is fused in a loop of a Mhyo membrane protein, preferably the membrane protein is selected from the group consisting of the P46 protein and the P97 protein, more preferably it is the P46 protein, preferably inserted between amino acids 92 and 93 of the P46 protein, wherein each of the DNA sequences is under the control of a promoter region of Mhyo selected between the promoter region of the P97 protein or of the Mhyo P46 protein, preferably the promoter region of the P46 protein. An example of this type of plasmid is that referred to as pTC3L and described in the Example section.

In these three preferred vectors, the group of exogenous DNA sequences, with the exception of the encoding sequences for the transposase, is flanked by two inverted repeats allowing the incorporation of said group to the genome of the Mhyo bacterium to be transformed. The inverted repeats preferably present the sequences SEQ ID NO: 7 for IRO and SEQ ID NO: 8 for IRI.

Another object of the invention is the use of the replicative plasmid vector and the transposon vector for preparing a mutant strain of Mhyo.

Strain of Mhyo

Any strain of Mhyo can be used in the method of the invention, i.e., the strain can be selected, among others, from field strains, Collection strains (for example, strain J or strain 232) or genetically modified strains.

The strain of Mhyo suitable for applying the method of the invention can be isolated from clinical or subclinical cases according to the usual methods used by the person skilled in the art, or it can be selected from the strains which are deposited in Type Culture Collections. In clinical cases, the strain presents the pathology typical of PEP, whereas in subclinical cases the strain is colonizing the animal mucous membranes but does not present any pathology. The strain of Mhyo that can be used to apply the method of the invention can show various degrees of virulence. A virulent strain or a strain expressing the main immunogenic determinants of Mhyo is preferably used in the method of the invention. The strains that can be used in the method of the invention include strain 232, the genome of which was described in the article by Minion et al., J. Bacteriol., 2004, 186(21), 7123-7133 and collected in the GenBank database with number AE017332; strain J, the genome of which was described in the article by Vasconcelos et al., J. Bacteriol., 2005, 187(16), 5568-5577, and collected in the GenBank database with number AE017243; or a wild type strain such as 6314, which corresponds to a virulent isolate of Mhyo belonging to Laboratorios Hipra, S. A. (Amer-Girona-Spain).

Transformation of the Strain

In the context of the invention, the expression "transforming a strain of Mhyo" has the usual meaning that is understood by a person skilled in molecular biology and it refers to a method by means of which a bacterium, in this case a Mhyo bacterium, incorporates an exogenous DNA sequence and said sequence performs a specific function.

The functions that the exogenous DNA sequence incorporated in the Mhyo bacterium can perform include, for example, RNA transcription, protein expression, recombination with other DNA sequences or interruption of the sequence coding for a gene in the genome of the host organism.

The method of transformation is one of the three methods by means of which an exogenous DNA sequence can be introduced in a bacterium. The other two are conjugation, which consists of transferring genetic material between two bacteria in direct contact, and transduction, which consists of injecting an exogenous DNA sequence into the bacterium by means of a bacteriophage virus.

The transformation of a bacterium can be carried out in the method of the invention by means of biochemical treatments known by the person skilled in the art such as, for example, incubation of the bacteria in the presence of a salt containing divalent ions, such as, for example, calcium chloride or calcium phosphate, exposure to a mixture of polyethylene glycol, incubation in the presence of polyvinyl alcohol, use of liposomes in which the exogenous DNA sequence is coated with a lipid, diethylaminoethyldextrane-mediated transfection, or by means of physical treatments such as electroporation, also referred to as electrotransformation, or by biolistics.

In the method of the invention, the bacterium is preferably transformed by incubating the bacteria in the presence of a salt containing divalent ions, exposing it to a mixture of polyethylene glycol, or subjecting it to electroporation; and it is more preferably carried out by electroporation.

Electroporation is a method well known by the person skilled in the art, the experimental protocol of which is described, for example, in the Sambrook and Russell manual, mentioned above.

In the electroporation process, a suspension of the bacteria in an electroporation buffer comprising the carrier vector carrying the exogenous DNA sequence is subjected to an electric pulse causing a change in the structure of the bacterial membrane for the purpose of facilitating the entrance of said sequence into the bacterium.

The electroporation buffer can be, for example, a buffer with pH 7.2 formed by sucrose and 4-(2-hydroxyethyl)-1-piperazineethanesulfonic acid (HEPES), although any buffer suitable for electroporation that is well known by the person skilled in the art can be used, such as those described in the Sambrook and Russell manual mentioned above.

The carrier vector carrying the exogenous DNA sequence is generally used at a concentration comprised between 0.1 and 5 μg/ml, preferably between 0.5 and 2 μg/ml. An electroporation buffer is typically used as a vehicle of said carrier vector.

The suspension of bacteria generally comprises between $10^6$ and $10^{12}$ cfu/ml.

Electroporation can generally be performed at a voltage comprised between 1 and 3 kV, a resistance comprised between 75 and 300Ω and a capacitance comprised between 10 and 40 μF. In the method of the invention, the electroporation is preferably performed at a voltage comprised between 2 and 3 kV, a resistance comprised between 100 and 175Ω, and a capacitance comprised between 20 and 30 μF.

In a preferred embodiment, before performing electroporation, the suspension of Mhyo bacteria is subjected to incubation in an electroporation buffer with a divalent ion chelating agent. Although said step is not fundamental in the method of the invention, it has been observed that it significantly increases transformation efficiency.

The chelating agents that can be used for said incubation include, for example, aminocarboxylic acids such as ethylenediaminetetraacetic acid (EDTA), nitrilotriacetic acid (NTA), diethylenetriaminepentaacetic acid (DTPA), or their alkaline salts; hydroxycarboxylic acids such as citric acid, gluconic acid, or their alkaline salts; phosphonic acids, such as 2-aminoethylphosphonic acid, 1-hydroxyethylidene-1,1-diphosphonic acid (HEDP), amino tris(methylenephosphonic acid) (ATMP), ethylenediaminetetra(methylenephosphonic) acid (EDTMP), or their alkaline salts. The chelating agent is preferably EDTA.

Once electroporation is performed, i.e., once the electric pulse is emitted, the suspension of bacteria is preferably incubated with an additional amount of the carrier vector comprising the exogenous DNA sequence.

The same amount of carrier vector that is added before emitting the electric pulse is normally used.

Said incubation is performed by incubating the suspension of bacteria and carrier vector with ice for a time period less than approximately 1 hour, and then keeping it for a time period comprised between 2 and 5 hours at a temperature of 37° C. and under a 5% carbon dioxide atmosphere.

In a more preferred embodiment, before performing electroporation, the suspension of Mhyo bacteria is subjected to incubation in an electroporation buffer with a divalent ion chelating agent, and after electroporation, the suspension of bacteria is incubated with an additional amount of the carrier vector comprising the exogenous DNA sequence.

In the method of the invention, the transformation can be carried out by using a replicative plasmid vector or by using a vector, preferably a plasmid, wherein at least one part thereof is incorporated by transposition.

Therefore, the transformation of the strain of Mhyo according to the method of the invention allows to obtain a strain of Mhyo comprising at least one exogenous DNA sequence inserted in its genome if the transformation has taken place by means of transposition or contains said DNA fragment in an extrachromosomal vector (or episomal element), which autonomously replicates stably in Mhyo, if the transformation has been performed by means of replicative plasmid vectors.

Obtaining Mutant Strains

An object of the invention is a mutant strain of Mhyo obtainable by the method of the invention.

Another object of the invention is a mutant strain of Mhyo comprising at least one exogenous DNA sequence stably incorporated in the genome or in the cytosol thereof. Preferably the exogenous DNA sequence is controlled by a DNA sequence, which has a degree of identity of at least 80%, preferably of at least 85%, more preferably of at least 90%, even more preferably of at least 95%, more preferably of at least 99%, and even more preferably 100% with a promoter region of Mhyo. In a preferred embodiment, the exogenous DNA sequence is comprised in the replicative plasmid vector of the invention.

In another preferred embodiment, the exogenous DNA sequence is comprised between IRI and IRO inverted sequence repeats of the transposon vector of the invention The mutant strain of Mhyo of the invention comprises the replicative plasmid vector of the invention or a substantial part of the transposon vector of the invention. When a replicative plasmid vector is used, the mutant strain of Mhyo comprises said vector in the cytosol thereof. In the case of using a transposon vector, the mutant strain of Mhyo incorporates a substantial part of the vector, which is that part comprised between the IRI and IRO inverted sequence repeats, and comprises at least one exogenous DNA sequence.

Another object of the invention is a strain of Mhyo transformed by the carrier vector of the invention.

In the context of the invention, "mutant strain of *Mycoplasma* hyopneumoniae" is understood as a strain of Mhyo which has been genetically modified by means of using genetic engineering tools.

A mutant strain of Mhyo stably incorporating an exogenous DNA sequence, which is functional in said mutant strain, can be obtained by the method of the invention.

In the context of the invention, it is understood that an exogenous DNA sequence is functional in a mutant strain of Mhyo when, for example, it expresses the protein coded by said sequence, transcribes RNA or genetically modifies said strain.

In the method of the invention for obtaining transformed strains of Mhyo, the starting material is preferably a Mhyo exponential growth phase culture.

Said culture is preferably obtained by using a culture medium comprising FriisHS medium (horse serum, yeast extract, heart infusion broth, Hank's balanced salt solution and PPLO (Pleuro-Pneumonia Like Organisms) broth).

The culture is preferably maintained between 48 and 144 hours at a temperature of approximately 37° C. under shaking between 100 and 200 rpm until reaching the exponential growth phase.

The bacteria are then isolated, preferably by centrifugation, and subjected to the method of transformation.

After transformation, the suspension of bacteria is preferably spread on plates of FriisHS medium supplemented with agar and the desired selective antibiotic The transformed colonies showing resistance to the antibiotic of the medium can be recovered after 2 or 3 weeks of incubation at a temperature of 37° C. and under a 5% carbon dioxide atmosphere. Said transformed colonies are then preferably inoculated in FriisHS medium supplemented with the selective antibiotic and after about 10 or 20 days the genotype and/or phenotype of the mutants obtained are studied by means of obtaining their genomic DNAs or protein extracts by methods well known by the person skilled in the art.

Transformed mutant strains of Mhyo expressing a recombinant protein can be obtained by the method of the invention.

In a preferred embodiment, the mutant strain of Mhyo of the invention expresses the content coded by the exogenous DNA sequence, for example, a protein. The exogenous DNA sequence can be, for example, circovirus (PCV2) capsid protein, or a Mhyo protein, for example, the P46 protein, to achieve over-expression thereof. Examples of them are the strains 232Cc6, 6314Cc1, 232Lc2 and 232Tc2, incorporating the exogenous DNA sequence in the genome of the bacterium.

An object of the invention is the mutant strain of Mhyo which was deposited by Laboratorios Hipra, S. A. (Amer, Girona, Spain) in Leibniz-Institut DSMZ (Deutsche Sammlung von Mikroorganismen und Zellkulturen GmbH, Inhoffenstraβe 7 B, 38124 Braunschweig, Germany) with the accession number DSM 26027 on 29 May 2012. Said strain, referred to as 232Cc6, incorporates the transposon present in plasmid pTC3C on Mhyo strain 232. This strain expresses the PCV2 capsid protein in the cytoplasm and in amounts which can be detected by Western blot and ELISA assay.

An object of the invention is the mutant strain of Mhyo which was deposited by Laboratorios Hipra, S. A. (Amer, Girona, Spain) in Leibniz-Institut DSMZ (Deutsche Sammlung von Mikroorganismen und Zellkulturen GmbH, Inhoffenstraβe 7 B, 38124 Braunschweig, Germany) with the accession number DSM 26020 on 29 May 2012. Said strain, referred to as 6314Cc1, incorporates the transposon present in plasmid pTC3C on the wild type Mhyo strain 6314. This strain expresses the PCV2 capsid protein in the cytoplasm and in amounts which can be detected by Western blot and ELISA assay.

An object of the invention is the mutant strain of Mhyo which was deposited by Laboratorios Hipra S. A. (Amer, Girona, Spain) in Leibniz-Institut DSMZ (Deutsche Sammlung von Mikroorganismen und Zellkulturen GmbH, Inhoffenstraβe 7 B, 38124 Braunschweig, Germany) with the accession number DSM 26033 on 29 May 2012. Said strain, referred to as 232Lc2, incorporates the transposon present in plasmid pTC3L on the wild type Mhyo strain 232. This strain expresses the PCV2 capsid protein in amounts which can be detected by ELISA assay.

An object of the invention is the mutant strain of Mhyo which was deposited by Laboratorios Hipra, S. A. (Amer, Girona, Spain) in Leibniz-Institut DSMZ (Deutsche Sammlung von Mikroorganismen und Zellkulturen GmbH, Inhoffenstraβe 7 B, 38124 Braunschweig, Germany) with the accession number DSM 26034 on 29 May 2012. Said strain, referred to as 232Tc2, incorporates the transposon present in plasmid pTC3T on the wild type Mhyo strain 232. This strain expresses the PCV2 capsid protein in amounts which can be detected by ELISA assay.

The following strains also express the protein coded by the exogenous DNA sequence, in that case incorporated in the cytosol of the bacterium as an episomal element:

- the transformed Mhyo strain 232POGc9 incorporating the replicative plasmid pOG on wild type Mhyo strain 232. Said incorporation has been detected by digesting the total DNA of this strain of Mhyo with restriction enzymes and analyzing the resulting fragments by agarose gel electrophoresis.
- the transformed Mhyo strain 232POGCREc1 incorporating the replicative plasmid pOGCRE on wild type Mhyo strain 232. The expression of the Cre recombinase is detected by means of Western blot and immunodetection.

Mutant strains of Mhyo, in which the exogenous DNA sequence incorporated by transposition produces an antisense RNA, which can block the translation of a gene responsible for the virulence of said strain, for example, a gene which corresponds to a Mhyo hemolysin, can be obtained by the method of the invention.

In a preferred embodiment, the mutant strain of Mhyo incorporates an exogenous DNA sequence in the genome or in the cytosol such that said strain produces an antisense RNA with respect to a gene responsible for the virulence of said strain.

Mutant strains of Mhyo, in which the exogenous DNA sequence incorporated by transposition in the genome of the strain interrupts a gene coding for a Mhyo virulence factor, can be obtained by the method of the invention and they show an attenuated virulence.

In a preferred embodiment, the mutant strain of Mhyo incorporates an exogenous DNA sequence which interrupts a gene coding for a Mhyo virulence factor, for example a hemolysin. One example is the strain referred to as 232TC3hlyC.

The mutant strains bearing an interrupted gene coding for a Mhyo virulence factor can be selected by means of methods well known by the person skilled in the art, such as sequencing the genome of said mutants.

An object of the invention is the mutant strain of Mhyo which was deposited by Laboratorios Hipra, S. A. (Amer, Girona, Spain) in Leibniz-Institut DSMZ (Deutsche Sammlung von Mikroorganismen and Zellkulturen GmbH, Inhoffenstraβe 7 B, 38124 Braunschweig, Germany) with the accession number DSM 26049 on 29 May 2012. Said strain, referred to as 232TC3hlyC, incorporates the transposon present in plasmid TC3 on the wild type Mhyo strain 232. This strain has an interruption of the ORF coding for the Mhyo hlyC virulence factor, so it is a good candidate for being used as an attenuated vaccine strain. The insertion in the genome is detected by means of Southern blot and by direct sequencing.

From the information contained in this description, the person skilled in the art can prepare other transformed strains of Mhyo by means of using the method of the invention and by selecting exogenous DNA sequences other than those specifically described.

An object of the invention is the use of a mutant strain of Mhyo comprising an exogenous DNA sequence in the cytosol or in the genome thereof as a host for the expression thereof. The exogenous DNA sequence can code for recombinant proteins or other sequences of interest as explained in this description.

It should be noted that mutant strains of Mhyo with very diverse characteristics can be obtained by the method of the invention, so that the person skilled in the art has at his/her disposition a method to genetically modify strains of Mhyo and to obtain strains bearing various functionalities.

Examples 5 and 6 show that the mutant strains of Mhyo obtained according to the method of the invention surprisingly stably incorporate the exogenous DNA sequence included in the carrier vector and express the content thereof such as, for example, by means of the production of recombinant proteins.

The strain obtained by the method of the invention can be attenuated or inactivated by means of standard procedures well known by the skilled person. In this way it can be used in the preparation of vaccines. Preferably it is used in inactivated form.

By the method of the invention, new strains of Mhyo are obtained hitherto undisclosed. Their features allow preparing new vaccines against Mhyo and at the same time against other pig pathogens. That is, the mutant strains of the invention allow preparing polyvalent vaccines by using a single strain transformed according to the method of the invention.

Vaccines

An object of the invention is a vaccine for protecting pigs against porcine enzootic pneumonia caused by Mhyo, and optionally against another disease or pathological conditions caused by microorganisms affecting pigs, comprising an immunologically effective amount of the mutant Mhyo strain of the invention.

In a preferred embodiment, the vaccine comprises a pharmaceutically acceptable vehicle and, optionally, an adjuvant agent.

The strain in the vaccine of the invention is inactivated or attenuated, preferably inactivated.

An inactivated vaccine may be obtained by inactivating a pathogenic agent, in that case a bacterium, usually through the use of heat; chemical compounds such as formaldehyde, BEI (binary ethyleneimine) or surfactants; mechanical force using a homogenizer, etc. The inactivation of the pathogenic agent may lead to maintenance of the structure thereof, but being unable to replicate, or to the destruction or disintegration of the structure. In the context of the invention, the term "inactivated vaccine" includes a composition comprising inactivated bacteria, but which retain their structure, as well as a composition in which the structure of the bacteria has been destroyed or disintegrated.

Another object of the invention is the use of the mutant Mhyo strain of the invention for preparing a vaccine against porcine enzootic pneumonia caused by Mhyo, and optionally against another disease or additional pathological conditions affecting pigs.

The expression "immunologically effective" means that the amount of bacteria administered in the vaccination process is sufficient to induce an effective immunological response in the host against an infection by the virulent forms of Mhyo and, in the event that the transformed strain of Mhyo expresses a recombinant protein which is capable of inducing or contributing to the induction of a protective response against diseases or pathological conditions which may affect pigs, it is also sufficient to induce an effective immunological response in the host against an infection caused by said microorganism.

The vaccine is preferably aimed at conferring protection to pigs against diseases or pathological conditions such as, for example, those caused by the *Actinobacillus* sp., *Brachyspira* sp., *Pasteurella multocida, Salmonella* sp., *Streptococcus* sp., *Isospora* sp., *Erysipelothrix rhusiopathiae, Leptospira* sp., *Staphylococcus* sp., *Haemophilus parasuis, Bordetella bronchiseptica, Clostridium* sp., *Mycoplasma* sp., *Lawsonia intracellularis, Escherichia coli* microorganisms, porcine reproductive and respiratory syndrome virus, swine influenza virus, contagious gastroenteritis virus, porcine parvovirus, encephalomyocarditis virus, coronavirus, rotavirus, porcine circovirus, porcine periweaning failure to thrive syndrome agent, classical swine fever virus, African swine fever virus, calicivirus and torque teno virus (TTV).

In a more preferred embodiment, the additional disease is that known as PCVAD (Porcine Circovirus Associated Diseases) caused by porcine circovirus (PCV2) whether it presents as a single agent or with the presence of other associated pathogens or microorganisms.

The vaccine of the invention can also be combined, in a single or different recipients, with an additional vaccine or antigenic composition. The additional vaccine or antigenic composition vaccine is preferably aimed at conferring protection to pigs against diseases or pathological conditions such as, for example, those caused by the *Actinobacillus* sp., *Brachyspira* sp., *Pasteurella multocida, Salmonella* sp., *Streptococcus* sp., *Isospora* sp., *Erysipelothrix rhusiopathiae, Leptospira* sp., *Staphylococcus* sp., *Haemophilus parasuis, Bordetella bronchiseptica, Clostridium* sp., *Mycoplasma* sp., *Lawsonia intracellularis, Escherichia coli* microorganisms, porcine reproductive and respiratory syndrome virus, swine influenza virus, contagious gastroenteritis virus, porcine parvovirus, encephalomyocarditis virus, coronavirus, rotavirus, porcine circovirus, porcine periweaning failure to thrive syndrome agent, classical swine fever virus, African swine fever virus, calicivirus and torque teno virus (TTV).

The vaccine of the invention comprises an immunologically effective amount of bacteria of an inactivated or live strain of Mhyo which can be obtained according to the method described in the present invention.

It is known that the dose to be used depends on the age and weight of the animal to be vaccinated and on the administration route.

Suitable doses are generally comprised in the range between $10^3$ and $10^{10}$ color changing units (ccu), preferably between $10^6$ and $10^{10}$ ccu, and more preferably between $10^8$ and $10^9$ ccu.

The animals can be vaccinated at any suitable time. A dose of the vaccine of the invention is preferably administered between 1 and 12 weeks of age, and more preferably the vaccine is administered starting from 3 weeks of age. In specific cases the administration of complementary doses to achieve a satisfactory protection may be necessary. Under these circumstances a second dose is preferably administered between 1 and 5 weeks after the first dose, more preferably after 3 weeks from the first dose. Preferably the vaccine is a single administration vaccine.

The vaccine of the invention is intended for porcine species including, among others, pigs, boars, sows, and piglets of any age or in any phase of their production cycle; it is preferably intended for pigs in the fattening stage, and more preferably for pigs from 1 to 12 weeks of life.

The vaccine can be administered intranasally, intradermally, mucosally or submucosally, subcutaneously, by means of aerosol, intramuscularly, or orally. Preferably it is administered intradermally or intramuscularly.

Said vaccine can be prepared according to the typical methods used by the person skilled in the art for preparing pharmaceutical formulations suitable for the different dosage forms, such as described, for example, in the manual *Remington The Science and Practice of Pharmacy,* $20^{th}$ edition, Lippincott Williams & Wilkins, Philadelphia, 2000 [ISBN: 0-683-306472].

The vaccines are typically prepared as injection vaccines in the form of solutions, emulsions or liquid suspensions. They can also be prepared in a solid form suitable to be dissolved or suspended in a liquid vehicle before injection.

The typical volume of a dose of an injection vaccine is between 0.1 ml and 5 ml, preferably between 0.15 ml and 3 ml, and more preferably between 0.2 ml and 2 ml. Usually in the intradermal administration it is used between 0.1 ml and 0.5 ml, preferably between 0.15 ml and 0.4 ml, and more preferably 0.2 ml. In the intramuscular administration, generally it is used between 0.5 ml and 5 ml, preferably between 1 ml and 3 ml, and more preferably between 1 ml and 2 ml.

To immunize an animal with the vaccine of the invention the mutant strain of Mhyo is commonly mixed with a pharmaceutically acceptable vehicle.

The liquid vehicles which can be used for preparing the vaccine include, for example, water, saline solution with a physiological salt concentration, or the culture liquid in which the bacteria are cultured.

Additionally, if desired, the vehicle can contain pharmaceutically acceptable excipients or auxiliary substances such as, for example, wetting agents, dispersing agents, emulsifying agents, buffering agents (for example, phosphate buffer), stabilizing agents such as carbohydrates (for example, glucose, sucrose, mannitol, sorbitol, starch, or dextrans), or proteins (for example, albumin, casein, bovine serum, or skimmed milk).

The physicochemical characteristics of the excipients as well as the name of the commercial products under which they are marketed can be found in the book by R. C. Rowe et al., *Handbook of Pharmaceutical Excipients,* $4^{th}$ edition, Pharmaceutical Press, London, 2003 [ISBN: 0-85369-472-9].

Adjuvants can also optionally be incorporated in the vaccine to enhance the effectiveness thereof. Preferably the vaccine of the invention further comprises an adjuvant.

Adjuvants are non-specific immune system stimulants which increase immunological response of the host against the invading pathogen. Examples of adjuvants are: aluminium hydroxide, aluminium phosphate, aluminium oxide, vitamin E, squalene, vegetable oil, saponins, ginseng, zymosan, glucans, dimethylaminoethyldextran, dextrans, nonionic block polymers, polyacrylate (carbomer), complete Freund's adjuvant, incomplete Freund's adjuvant, muramyl dipeptides, W/O, O/W, W/OW type emulsions, and mixtures thereof.

In a preferred embodiment the vaccine is an injection vaccine and comprises the mutant strain of the invention inactivated by a non-ionic surfactant. Preferably it is used a non-ionic surfactant selected from the group formed by alkylphenol ethoxylates, ethoxylated sorbitan esters, ethoxylated fatty alcohols, ethoxylated fatty acids, fatty acid alkanolamides, ethoxylated fatty acid alkanolamides, ethoxylated fatty amines, fatty amine oxides, fatty amidoamine oxides, fatty acid glycerides, sucrose esters, alkyl polyglycosides, ethylene oxide and propylene oxide copolymers, and ethoxylated and propoxylated fatty alcohols; more preferably it is selected from alkylphenol ethoxylates and ethoxylated sorbitan esters, and yet more preferably it is an alkylphenol ethoxylate, such as Triton® X-100 marketed by Dow, for example.

In a more preferred embodiment, the vaccine is an injection vaccine and comprises the mutant strain of the invention inactivated by a non-ionic surfactant and as an adjuvant, a W/O/W type emulsion, such as the product Montanide® ISA 201 marketed by the company SEPPIC (France), for example.

In a preferred embodiment the vaccine can comprise the strain of the invention in a lyophilized form. The lyophilization process is carried out by means of methods well known by the person skilled in the art.

Vaccination Kit

The object of the present invention also includes a vaccination kit for vaccinating pigs against an infection or a disease caused by Mhyo and optionally against another disease or pathological conditions caused by microorganisms affecting pigs.

Said vaccination kit comprises a container comprising an immunologically effective amount of the mutant strain of the invention or a vaccine of the invention.

In another embodiment, the vaccination kit comprises a combination of the vaccine of the invention with an additional antigenic composition, which are contained in a single recipient or in different recipients. Such additional antigenic composition is aimed at conferring protection to pigs against diseases or pathological conditions such as those mentioned in the Vaccines section.

The industrial application of the invention is clearly inferred from the description. It should be pointed out that PEP is a widespread global chronic respiratory disease responsible for great economic losses in the pig industry and that the possibility of genetically modifying strains of Mhyo in a targeted and stably manner allows the preparation of vaccines with superior properties than those of conventional bacterins. Attenuated mutant strains of Mhyo, mutant strains over-expressing a specific virulence factor, strains inhibiting a specific virulence factor, or strains further expressing antigenic components of microorganisms responsible for diseases affecting pigs, for example, which are suitable for preparing effective vaccines against PEP and against other porcine pathologies, can be prepared by means of the method of the invention.

The targeted genetically modification of Mhyo in stable form for the first time, has allowed the inventors, inter alia, the use of these transformed strains as expression vector of exogenous DNA sequences like, for example, nucleotide sequences coding for proteins of therapeutic or preventive interest such as the protein of the PCV2 capsid, among others. By means of the technology disclosed in this invention, new vaccine polyvalent candidates have been designed and prepared, which can be used to prevent different diseases at the same time by administering a single strain.

Assay for the Production of Recombinant Proteins by Transformed Strains of Mhyo According to the Method of the Invention The ELISA method can be used to identify the presence of the protein expressed by the exogenous DNA sequence in the mutant strains of Mhyo of the invention.

In particular, to detect the presence of the PCV2 capsid protein and to quantify it in the strains of Mhyo obtained, a commercial kit, which allows detecting and estimating in an approximate manner the amount of said antigen by means of plate immunodetection (ELISA), was used.

The protein extracts were obtained after concentrating them in exponential-phase cultures of each strain and lysing the cells obtained.

The results were positive indicating that the proteins coded by ORF2 or ORF2v2 are expressed at a greater or lesser amount in all the assayed strains and plasmids (FIG. 5B).

The strains with the version originating from plasmid pTC3C were also analyzed by means of denaturing polyacrylamide gel electrophoresis and Western blot (FIG. 5C). Bands of the same molecular weight as the PCV2 capsid protein were detected.

It can be observed that proteolytic degradation bands, a common problem in recombinant protein expression, did not appear in the electrophoresis gels.

To that end, the PCV2 capsid protein expressed in a recombinant manner in Mhyo can be a good antigen for formulating a polyvalent vaccine. Likewise, Mhyo is a good host for the recombinant production of proteins.

Vaccination Assays

The effectiveness of the vaccines containing the mutant strains of Mhyo obtained according to the method of the invention was tested, wherein said strains comprised the exogenous DNA sequence coding for the PCV2 capsid protein in the genome of the bacteria, and they expressed said protein in the cytosol of the bacteria.

To that end, vaccines containing strains 6314Cc1 or 232Cc6 were tested, and the animals were vaccinated with a single dose or were revaccinated with a second dose, as described in the Examples section.

Additionally, two groups of animals were incorporated in the study: a non-vaccinated, but infected group (group 5), and a non-vaccinated and non-infected group (group 6).

The following responses were assessed: the immunological response against Mhyo, the immunological response against PCV2, and the PCV2 viral DNA load in the serum of the animals.

By observing the results of the vaccination assays performed with the vaccines comprising mutant strains of Mhyo obtained according to the method of the invention shown in FIGS. 6, 7 and 8, it can be concluded that the transformed strains of Mhyo expressing the PCV2 capsid protein generate a significant immunological response against Mhyo and, surprisingly, also against PCV2, significantly reducing PCV2 viral load such that they can be used in vaccines against infections caused by Mhyo and by PCV2 at the same time.

A vaccine containing a mutant strain of Mhyo obtained according the method of the invention was also tested against an infection by PCV2 and Mhyo, wherein such strain comprised the exogenous DNA sequence coding for the PCV2 capsid protein in the genome of the bacterium, and expressed such protein in the cytosol of the bacterium.

It was tested a vaccine containing the 6314Cc1 strain, animals were vaccinated with a single dose and were challenged with a PCV2 isolate and with a pathogenic strain of Mhyo, as described in the Examples.

Additionally, two groups of animals were incorporated in the assay: a non-vaccinated but infected (group 2), and a non-vaccinated and non-infected (group 3). The responses assessed were: the immunological response against Mhyo, the immunological response against PCV2, the PCV2 viral DNA load in the serum of animals, and the Mhyo-like lesions in the lungs of animals.

It was observed that the strain of Mhyo, genetically modified according to the method of the invention, which expresses the capsid protein of PCV2, generates a significant reduction of the PCV2 viral DNA load and of the Mhyo-like lesions in the lungs of animals compared with the non-vaccinated animals.

A vaccine containing a mutant strain of Mhyo obtained according the method of the invention was also tested, wherein such strain comprised a replicative plasmid vector comprising the exogenous DNA sequence coding for the PCV2 capsid protein and expressed such protein in the cytosol of the bacterium. As in the previous tests, it was observed that the strain of Mhyo, genetically modified according to the method of the invention by means of replicative plasmids, which expresses the PCV2 capsid protein, generates a significant reduction in the PCV2 viral load.

Testing the Degree of Attenuation of Mutant Strains

The mutants obtained upon putting the method of the invention for transforming strains of Mhyo into practice include strain 232TC3hlyC containing the plasmid pTC3 incorporated by transposition in the region of the genome coding for a Mhyo virulence factor: hemolysin C, coded by the hlyC gene.

To assess the attenuation degree of said strain, 8 week-old pigs were selected and divided into two groups of 8 animals per group. The first group was intratracheally infected with a dose of strain 232TC3hlyC, and the second group with a dose of the wild type strain of Mhyo, Mhyo strain 232, before being modified.

The animals were euthanized 28 days after the infection and it was observed that no colonization occurred in the nasal area in any of the two groups of animals, whereas 25% of the animals from the group infected by the wild type strain showed bronchial colonization.

None of the animals infected with the transformed strain of Mhyo showed bronchial colonization.

Therefore, the transformed Mhyo strain 232TC3hlyC shows attenuation in relation to the wild type parental strain and it can be used, as such, as a vaccination candidate in an attenuated live vaccine.

The Mhyo mutant strain 6314POGAc4 was obtained by the method of the invention. Said mutant strain inhibits the expression of Mhyo hemolysin 159 gene, since the exogenous DNA sequence incorporated by means of a replicative plasmid (pOGA159) produced an antisense RNA corresponding to a gene coding for a Mhyo hemolysin. When the animals were infected with this strain, it was observed that the strain showed attenuation with respect to the wild type parental strain. Said mutant strain was characterized by a reduced ability to colonize the upper and lower respiratory tract, as well as by a reduced capacity to cause lesions typical of PEP.

The following examples are set out to provide the person skilled in the art with a sufficiently clear and complete explanation of the present invention, but they must not be considered as limiting the essential aspects of the object thereof set out in the preceding sections of this description.

EXAMPLES

The recombinant DNA techniques and methods applied below are described in detail in the manuals by Sambrook and Russell, *Molecular Cloning* 3rd Ed. Cold Spring Harbor Laboratory Press, Cold Spring Harbor N.Y. 5 (2001) and by Ausubel et al., *Current Protocols In Molecular Biology*, John Wiley and Sons, Inc. (1998).

*E. coli* XL1-blue strain (Stratagene) has been used as the host for the vectors based on plasmids pMTn4001 or pBluescript II SK.

Unless otherwise indicated, all the DNA sequences described in the plasmid constructs described in this section come from the sequence deposited in the GenBank database with number AE017243. This genomic sequence corresponds to that of Mhyo strain J described by Vasconcelos et al., J. Bacteriol., 2005, 187(16), 5568-5577.

All the oligonucleotide sequences described below are written in 5' to 3' direction unless otherwise indicated. Phusion thermopolymerase (Finnzymes) having proof reading activity was used in all PCR reactions.

The underlined oligonucleotide sequences indicate the presence of a restriction enzyme site which is specified in the name of each of the sequences.

Example 1

Choosing a Strain of Mhyo

The wild type strains of Mhyo used were strain 6314 corresponding to a virulent Mhyo isolate from Laboratorios Hipra S. A. (Amer-Girona-Spain) and Strain 232 from Iowa State University (Ames-Iowa-USA).

Example 2

Construction of Replicative Plasmids

Example 2.1

Construction of Replicative Plasmid pOG

Figure 1:
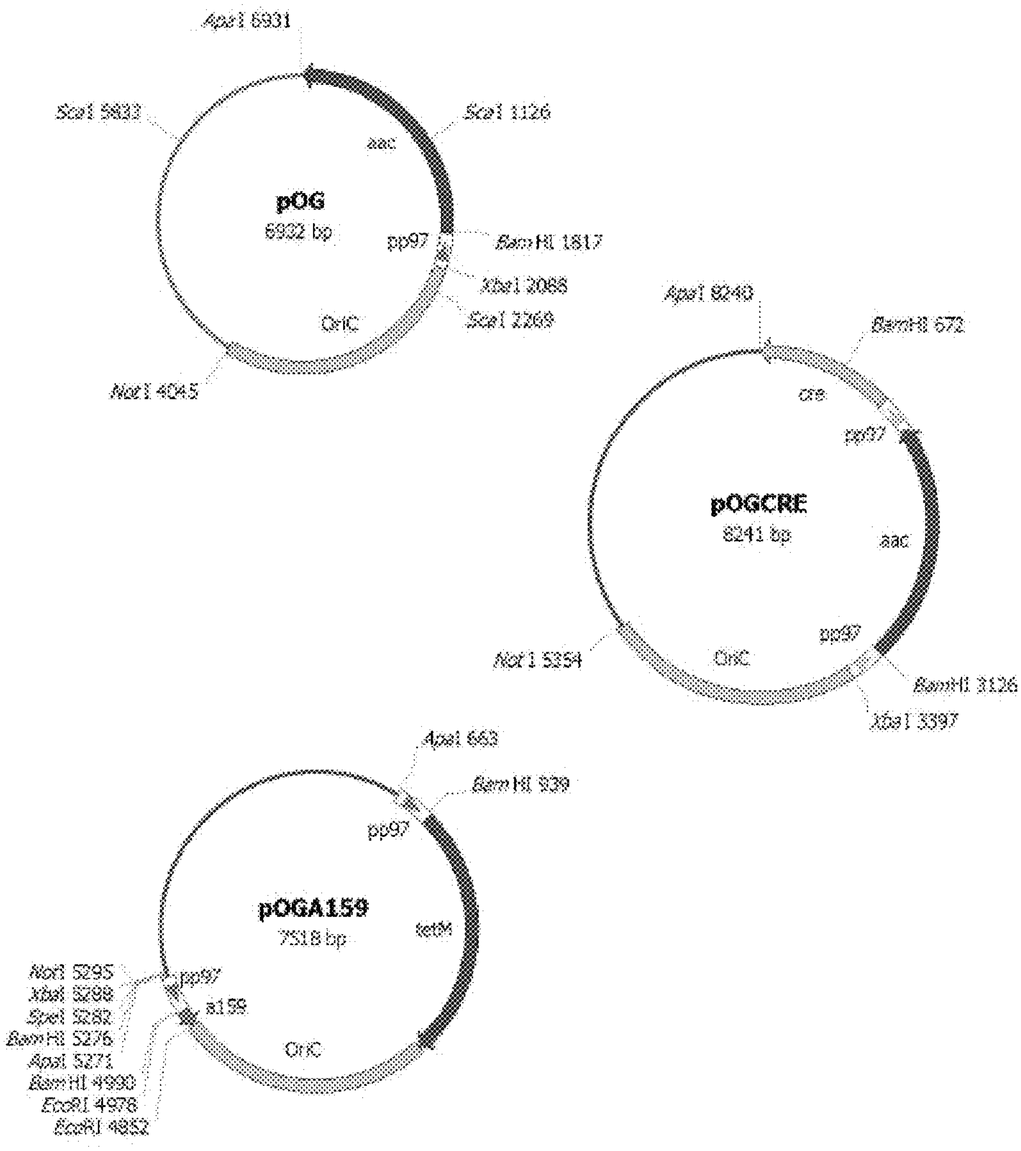
FIG. 1 shows a diagram of the replicative plasmids used to genetically modify Mhyo and achieve the production of recombinant proteins or antisense transcripts. The promoters, the genes and the restriction enzyme sites used for cloning operations are indicated by arrows.

To obtain a replicative plasmid in Mhyo, the oriC region of Mhyo amplified by means of PCR was introduced in a plasmid pBluescript II SK. The oligonucleotides 5OriCNotI (ATG CGC GGC CGC TTA TTT ATC AGA AAC AGT TAG) (SEQ ID NO: 9) and 3OriCXbaI (AGT CGG GCC CAG CTT GCG CAT CAT TGG ATG ATG GAT TC) (SEQ ID NO: 10) were used for this amplification and the genomic DNA of Mhyo strain J was used as a template. The 1.96 kb fragment obtained was then digested with restriction enzymes NotI and XbaI. On the other hand, the gentamicin resistance gene (aac(6')-aph(2")) was amplified by PCR by means of oligonucleotides 5GmORF (ACT GGG ATC CAT GAA TAT AGT TGA AA ATG) (SEQ ID NO: 11) and 3GmApa (GGA TGG GCC CAG CTT GCG CAT CAT TGG) (SEQ ID NO: 12) and using plasmid pIV-T as a template. The 1.8 kb PCR product was then digested with the corresponding restriction enzymes. The promoter region of the gene of the P97 protein was amplified by PCR by means of oligonucleotides 5'p97XbaI (G ATC TCT AGA TCG AGG AAG ACT GAT TAG AAA TTT AGA ACT) (SEQ ID NO: 13) and 3'p97BamHI (GAT CGG ATC CAC TCA TAT TTT AAA CCT CAA TTA T) (SEQ ID NO: 14) using DNA of Mhyo strain J as the template. The PCR product (266 bp) was then digested with the corresponding restriction enzymes. Finally, the three fragments obtained were ligated in plasmid pBluescript II SK previously digested with the restriction enzymes XbaI and BamHI and the ligation mixture was transformed into *Escherichia coli* XL1-blue cells. Colonies bearing the desired construct were identified from the colonies resulting from the transformation by means of restriction pattern analysis and sequencing. One of the positive clones was named pOG and selected for the next steps (FIG. 1).

Example 2.2

Construction of Replicative Plasmid pOGCRE

Replicative plasmid pOGCRE was obtained by digesting plasmid pOG with restriction enzymes BamHI and ApaI and recovering a 5.1 kb fragment. On the other hand, the gentamicin resistance gene (aac(6')-aph(2")) was amplified by means of PCR from plasmid pIV-T using oligonucleotides 5GmORF and 3GmORFSpeI (ACT GAC TAG TAG CTT GCG CAT CAT TGG) (SEQ ID NO: 15) a 1.8 kb fragment which was then digested with restriction enzymes BamHI and SpeI being obtained. The gene corresponding to Cre recombinase was amplified by means of PCR using plasmid pSH62 (Euroscarf) and oligonucleotides 5CreBglII (ATG CAG ATC TAT GTC CAA TTT ACT GAC CGT ACA CCA AAA TTT G) (SEQ ID NO: 16) and 3CreApaI (ATG CGG GCC CTTA ATC GCC ATC TTC CAG CAG GCG CAC) (SEQ ID NO: 17) as the template. The PCR product (1.0 kb) was cleaved with the enzymes BglII and ApaI. Lastly, the plasmid pOG was digested again, this time with restriction enzymes BamHI and XbaI, and it was recovered a band of 266 bp corresponding to the promoter of the gene of the P97 protein. The four fragments obtained were ligated by means of T4 DNA ligase and the ligation reaction was transformed into *E. coli* XL1-blue cells. From the resulting transformation colonies the ones bearing the desired construct were identified by means of restriction pattern analysis. One of the positive clones named pOGCRE was selected for the next steps (FIG. 1).

Example 2.3

Construction of Replicative Plasmid pOGC

To obtain plasmid pOGC, plasmid pBluescript II SK was digested with the enzyme NotI, and once purified it was dephosphorylated with alkaline phosphatase enzyme. At the same time, a 992 bp fragment was obtained by digesting the synthetic gene ORF2v2 (SEQ ID NO: 5) with restriction enzymes SpeI and NotI. Using plasmid pOGCRE as a template, a DNA segment was amplified with oligonucleotides 3gmORFSpeI and 5OriCNotI by means of PCR and once purified, the PCR product was digested with enzymes SpeI and NotI. The three fragments obtained were ligated by means of T4 DNA ligase and the ligation reaction was transformed into *E. coli* XL1-blue cells. The positive clones were identified by means of restriction mapping and sequencing (FIG. 2).

Example 2.4

Construction of Replicative Plasmid pOGL

To obtain plasmid pOGL, plasmid pOGC was digested with enzymes NotI and SpeI and bands of 2.8 kb and 4 kb were recovered. The DNA fragment corresponding to the band of 2.8 kb was dephosphorylated with alkaline phosphatase. At the same time, a 2.25 kb fragment was obtained by digesting the plasmid pTC3L (see Example 3.4) with restriction enzymes SpeI and NotI. The three fragments obtained were ligated by means of T4 DNA ligase and the ligation reaction was transformed into *E. coli* XL1-blue cells. The positive clones were identified by means of restriction mapping and sequencing (FIG. 2).

Example 2.5

Construction of Replicative Plasmid pOGT

To obtain plasmid pOGT, plasmid pOGC was digested with enzymes NotI and SpeI and bands of 2.8 kb and 4 kb were recovered. The DNA fragment corresponding to the band of 2.8 kb was dephosphorylated with alkaline phosphatase. At the same time, a 2.23 kb fragment was obtained from the digestion of plasmid pTC3T (see Example 3.5) with restriction enzymes SpeI and NotI. The three fragments obtained were ligated by means of T4 DNA ligase and the ligation reaction was transformed into *E. coli* XL1-blue cells. The positive clones were identified by means of restriction mapping and sequencing (FIG. 2).

Example 2.6

Construction of Replicative Plasmid pOGA159

Replicative plasmid pOGA159 was constructed in two consecutive cloning steps. By means of a PCR reaction with oligonucleotides 5'p97ApaI and 3TetMClaI (TGT TAT CGA TACO GTC GAT GCA CCT CGA GCT AAG TTA TTT TAT TG) (SEQ ID NO: 18) and using plasmid pMTn4001 as a template, a 2.2 kb fragment corresponding to the promoter of the gene of P97 protein was amplified. This PCR product was digested with restriction enzymes ClaI and ApaI. On the other hand, and using plasmid pOG as a template, a 1.9 kb fragment was amplified with oligonucleotides 5OriCClaI (AGA CAT CGA AAG CTT GAT TAT GCT GAT TGC ATT CTT TCA ATT TG) (SEQ ID NO: 19) and 5OriCEcoRI (AGA GGA AT CC GAT TTA TTT ATC AGA AAC AGT TAG TCT TTT CC) (SEQ ID NO: 20) corresponding to the Mhyo oriC. This PCR product was digested with restriction enzymes EcoRI and ClaI. Subsequently, by means of PCR a 316 bp fragment corresponding to the promoter of P97 protein gene was amplified with oligonucleotides 5XbaIpp97 (AGA CTC TAG AAC TAG TGG ATC CCC CGG GCC CCT CGA GGA AGA CTG ATT AGA AAT TTA G) (SEQ ID NO: 21) and 3EcoRIpp97 (AGA CGA ATT CGA ATT CCT GCA GGG ATC CAC TCA TAT TTT AAA CCT C) (SEQ ID NO: 22). Once purified, this fragment was digested with enzymes EcoRI and BamHI. The last step of this first cloning process was digest plasmid pBluescript II SK with restriction enzymes XbaI and ApaI. These four DNA fragments were ligated by means of T4 DNA ligase and the ligation reaction was transformed into *E. coli* XL1-blue cells. Colonies bearing the desired construct were identified from the colonies resulting from the transformation by means of restriction pattern analysis. The new plasmid thus obtained was digested with restriction enzyme EcoRI. Lastly the DNA designed for silencing was amplified by PCR with oligonucleotides 5ahlycEcoRI (CAT CGA ATT CAC GAA TTA GTG ATT CTG CCT TTT C) (SEQ ID NO: 23) and 3ahlycEcoRI (CAT CGA ATT CAT TAA AGT TGA TTC GGT GTT TAA TC) (SEQ ID NO: 24). Once digested with restriction enzyme EcoRI and dephosphorylated by means of alkaline phosphatase, DNA fragments obtained were ligated by means of T4 DNA ligase and the ligation reaction was transformed into *E. coli* XL1-blue cells. Colonies bearing the desired construct were identified from colonies resulting from the transformation by means of sequencing (FIG. 1).

Example 3

Construction of Plasmids for Transformation by Transposition

Example 3.1

Construction of Plasmid pTC3 for Transformation by Transposition

Plasmid pMTn4001 (Pich et al., Microbiology 152:519-527 (2006)) was amplified by PCR with oligonucleotides 5pMTn4001 PstI (CAT GCT GCA GCC CGG GGG ATC CAC TAG TTC TAG AG) (SEQ ID NO: 25) and 3pMTn4001 (GTA CCC AAT TCG CCC TAT AGT GAG TCG) (SEQ ID NO: 26). Oligo 3pMTn4001 was phosphorylated at its 5' end. The product of this PCR reaction (2.98 kb) was digested with restriction enzyme PstI. On the other hand, the promoter of the gene of P97 protein was amplified by means of PCR with oligonucleotides 5'p97 (TCG AGG AAG ACT GAT TAG AAA TTT AGA ACT) (SEQ ID NO: 27) and 3'p97BamHI using the DNA of Mhyo Strain J as a template. This PCR product (280 bp) was digested with restriction enzyme BamHI and dephosphorylated with alkaline phosphatase. The same promoter was also amplified by means of a second pair of oligonucleotides: 5'p97ApaI (GAT CGG GCC CTC GAG GAA GAC TGA TTA GAA ATT TAG AAC T) (SEQ ID NO: 28) and 3'p97BamHI and digested with restriction enzymes ApaI and BamHI. The transposase gene was amplified by means of PCR using plasmid pMTn4001 as a template and oligonucleotides 5'TnpBamHI (GAT CGG ATC CAT GAC CCA AGT ACA TTT TAC ACT GAA AAG) (SEQ ID NO: 29) and 3'TnpApaI (GAT CCT CGA GGG GGG GCC CTT TTA CAC AAT TAT ACG GAC) (SEQ ID NO: 30). The obtained band of 978 bp was then digested with restriction enzymes BamHI and ApaI. Lastly, the fragment corresponding to tetracycline resistance tetM was amplified from plasmid pMTnTetM438 (Pich et al., Microbiology 152:519-527 (2006)) using the oligonucleotides 5'TetMBamHI (GAT CGG ATC CAT GAA AAT TAT TAA TAT TGG AGT T) (SEQ ID NO: 31) and 3' TetMPstI (GAT CGC TGC AGG AAT TCG ATA TCA AGC TTA TCG ATA CCG TCG ATG CAC CT) (SEQ ID NO: 32). The 1.9 kb fragment obtained was digested with restriction enzymes SalI and BamHI and dephosphorylated with alkaline phosphatase. The five resulting fragments were ligated by means of T4 DNA ligase and the ligation reaction was transformed into *E. coli* XL1-blue cells. From the resulting transformation colonies the ones bearing the desired construct were identified by means of restriction pattern analysis and sequencing. One of the positive clones named pTC3 was selected for the next steps (FIG. 3).

Example 3.2

Construction of Plasmid pTC366 for Transformation by Transposition

This plasmid is directly derived from pTC3 by the inclusion of two 34 bp lox66 sequences (ATA ACT TCG TAT AGC ATA CAT TAT ACG AAC GGT A) (SEQ ID NO: 33) flanking the tetracycline resistance gene. To that end, the tetracycline resistance gene sequence TetMp97 of plasmid TC3 was amplified by PCR with oligonucleotides 5loxp66Tetp97 (GAT TAA GGG CCC ATA ACT TCG TAT AGG ATA CTT TAT ACG AAG TTA TGT CGA CCC CCT CGA GGA AGA CTG) (SEQ ID NO: 34) and 3loxp66Tetp97 (GGG ACT AGT TAC GGT TCG TAT AAT GTA TGC TAT ACG AAG TTA TCT GCA GGA TAT CAA GCT TAT CGA TAC CGT CG) (SEQ ID NO: 35), obtaining a 2.2 kb PCR fragment which was digested with restriction enzymes ApaI and SpeI. At the same time, plasmid TC3 was digested with the same restriction enzymes and the band of 4.4 kb was recovered. The two fragments were ligated using T4 DNA ligase and the ligation mixture was transformed into *E. coli* XL1-blue cells. A positive clone, which had correctly incorporated lox66 sequences and which was called pTC366 (FIG. 3), was identified by sequencing from the colonies resulting from the transformation.

Example 3.3

Construction of Plasmid pTC3C for Transformation by Transposition

To obtain plasmid pTC3C, plasmid pTC366 was digested with enzymes SpeI and NotI. A 992 bp fragment originating from the digestion of synthetic gene ORF2v2 (SEQ ID NO: 5) with the same restriction enzymes was cloned on this plasmid. The positive clones were identified by means of restriction mapping (FIG. 3).

Example 3.4

Construction of Plasmid pTC3L for Transformation by Transposition

By means of a PCR reaction with oligonucleotides P46CtFdHindIII (GTG TAA GCT TAA AAA CCA GGA TGC ACA AAA TAA C) (SEQ ID NO: 36) and P46CtRv-NotI (TGT TGC GGC CGC TTT AGG CAT CAG GAT TAT CAA C) (SEQ ID NO: 37) and using the genomic DNA of strain 232 as a template, a 1.0 kb fragment corresponding to the 3' end of the gene of P46 protein was amplified. This PCR product was digested with restriction enzymes HindIII and NotI. On the other hand, and by using the same genomic DNA as a template, a 276 bp fragment was amplified with oligos P46NtFdSpeI (AGA CAC TAG TTT GAA TTT GTA TTT TCC ATA ATC) (SEQ ID NO: 38) and P46NtRvBamHI (AGA GGG ATC CTG TAA TTG TTG AAG TTG CTG CCT) (SEQ ID NO: 39). This fragment corresponding to the promoter and to the 5' end of P46 protein gene was then digested with restriction enzymes SpeI and BamHI. Lastly, and by using as a template plasmid pTC3C together with oligonucleotides CircRv-NotI (TGT TGC GGC CGC TTA TGG TTC TAA 55 TGG TGG ATC) (SEQ ID NO: 40) and Circ2Fd-BamHI (GTG TGG ATC CAT GAC ATA TCC AAG AAG AAG AT) (SEQ ID NO: 41), the gene corresponding to PCV2 capsid protein was amplified. This 712 bp DNA fragment was then digested with restriction enzymes NotI and BamHI. All the fragments obtained were cloned in plasmid pTC366 previously digested with enzymes SpeI and NotI. The positive clones were identified by means of restriction mapping (FIG. 3).

Example 3.5

Construction of Plasmid pTC3T for Transformation by Transposition

In this example, oligonucleotides P46NtFdSpeI and P46CIRCRv (ATC TTC TTC TTG GAT ATG TCA TGG CAT CAG GAT TAT CAA CAT TA) (SEQ ID NO: 42) were used for the PCR amplification of the promoter region and the 5' end of the coding region of the gene of P46 protein starting from the genomic DNA of strain 232. The band of 1.25 kb obtained was cleaved with restriction enzyme SpeI. At the same time a second PCR reaction was performed with oligonucleotides P46CIRCFd (TAA TGT TGA TAA TCC TGA TGC CAT GAC ATA TCC AAG AAG AAG AT) (SEQ ID NO: 43) and CircRv-NotI on pTC3C obtaining a 732 bp DNA fragment. By means of a recombinant PCR reaction in which the preceding fragments were used as a template and using the oligonucleotides P46NtFdSpeI and CircRv-NotI, a 2.2 kb fragment was obtained. This fragment was digested with restriction enzymes SpeI and NotI and ligated with plasmid pTC366 previously digested with enzymes SpeI and NotI. The positive clones were identified by means of restriction mapping and sequencing (FIG. 3)

Example 4

Obtaining Transformant Bacteria

All the products and reagents used in this method were sterilized by means of autoclaving, filtration or irradiation. The starting material was a Mhyo culture in exponential growth phase. This growth phase is preferably obtained by using a 1/100 dilution of the inoculum and leaving the culture to grow for about 48-144 hours in FriisHS medium (20% (v/v) irradiated horse serum, 2.4% (v/v) yeast extract, 0.1% (v/v) phenol red, 0.4% “Hanks’ Balanced salt solution”, 0.058% (w/v) “Heart Broth Infusion”, 0.054% (w/v) PPLO and ampicillin at a final concentration of 100 μg/ml). Once about 40 ml of Mhyo culture in stationary phase were obtained, the content of the culture flasks was pipetted 10 times to separate the cells and the culture was then filtered with a 0.45 μm filter to finish separating the cells. The cells were then centrifuged for 20 minutes at 20,000×g, resuspended in an electroporation buffer (272 mM Sucrose, 200 mM Hepes pH 7.2) supplemented with 1 mM EDTA and were incubated in ice for 10 minutes. After 10 minutes of incubation with EDTA the centrifugation was repeated at 20,000×g for 20 minutes and the cells were resuspended in a volume between 100 and 300 μl of electroporation buffer. 20 μg of plasmid previously dissolved in electroporation buffer at a concentration between 0.5 and 2 $\mu g \cdot ml^{-1}$ and the cell suspension up to a final volume of 100 μl were added into a 0.2 cm electroporation cuvette. When performing the electroporation, the variables of the electroporation machine were set to a voltage of 2.5 kV, resistance between 100 and 175Ω and capacitance of 25 μF. The typical “time constant” values obtained were between 2.3 and 3 ms. Once the electric pulse was emitted, 900 μl of FriisFBS medium (exactly the same formulation as the FriisHS medium, but replacing the horse serum with fetal bovine serum) and additional 20 μg of plasmid were added. The resulting suspension was incubated for 20 minutes on ice and then 3 hours at 37° C. and 5% $CO_2$. After 3 hours, the suspension obtained was distributed (about 200 μl per plate) on FriisHS plates supplemented with 0.7% (w/v) low melting point agar and the desired selective antibiotic (0.5 μg/ml tetracycline and/or 10 μg/ml gentamicin).

After 2 or 3 weeks of incubation at 37° C. and 5% CO2, the transformant colonies in the Friis HS plates were recovered and inoculated in 50 ml flasks containing 10 ml of FriisHS medium supplemented with the selective antibiotic at the previously indicated concentrations. Once the medium changed its color (between 10 and 20 days after incubation at 37° C. and 150 rpm) genotypic and/or phenotypic studies of the obtained mutants were conducted by obtaining genomic DNAs or protein extracts as it is known by any person skilled in the art.

Examples 4.1. to 4.8

Obtaining Transformed Mutant Strains of Mhyo

By substantially following the method described in Example 4, the transformed mutant strains of Mhyo shown in Table I were prepared using the plasmids which are also listed in the same table.

TABLE I

| Example | Plasmid | Parental strain | Transformed mutant strain |
|---|---|---|---|
| 4.1 | pTC3C | 232 | 232Cc6 |
| 4.2 | pTC3C | 6314 | 6314Cc1 |
| 4.3 | pTC3L | 232 | 232Lc2 |
| 4.4 | pTC3T | 232 | 232Tc2 |
| 4.5 | pTC3 | 232 | 232TC3hlyC |
| 4.6 | pOG | 232 | 232POGc9 |
| 4.7 | pOGCRE | 232 | 232POGCREc1 |
| 4.8 | pOGA159 | 6314 | 6314POGAc4 |

The mutant strains shown in the table were selected from different mutants obtained in the transformation carried out according to the method of the invention. These strains were used in different vaccination and attenuation degree assays.

Example 5

Analysis of the Mutant Strains Obtained by Transformation with Replicative Plasmids Example 5.1

Analysis of the Mutant Strains Obtained by Transformation with Replicative Plasmid pOG The transformed strain in Example 4.6, 232POGc9, was used to confirm the presence of the plasmid in the cells recovered from the transformation of Friis agar plates and grown in FriisHS medium with 10 μg/ml gentamicin.

To that end, total DNA was purified from the cells. The DNA obtained was digested with restriction enzyme ScaI, which in this case results in the appearance of bands that can be easily identified in an agarose gel (FIG. 4A).

The appearance of bands corresponding to the plasmid which clearly stand out over the genomic DNA background indicate that the clone analyzed contains the plasmid and that this plasmid stably replicates to give rise to 25-30 copies of plasmid per cell.

The analysis of the results shows that the replicative plasmids of the invention stably propagate to the progeny of the transformed bacteria.

Example 5.2

Analysis of the Mutant Strains Obtained by Transformation with Replicative Plasmid pOGCRE The transformed strain in Example 4.7, 232POGCREc1, includes the gene coding for Cre protein.

To check whether the introduction of heterologous genes by means of replicative plasmids gave rise to the expression of corresponding proteins in a detectable manner in Mhyo, a total protein extraction from the clones recovered in the transformation assays with plasmid pOGCRE was analyzed by denaturing polyacrylamide gel electrophoresis and, subsequently, a Western-blot was performed to detect the presence of Cre recombinase by immunological methods (FIG. 4B).

In this case, the Cre protein was only detected in the strain which has been transformed with plasmid pOGCRE, thus showing the usefulness of the replicative plasmids for the heterologous expression of proteins in Mhyo.

Example 5.3

Analysis of the Mutant Strains Obtained by Transformation with Replicative Plasmid pOGA159

The transformed strain in Example 4.8, 6314pOGAc4, was used to confirm the presence of the plasmid in the cells recovered from the transformation of Friis agar plates and grown in FriisHS medium with 0.5 μg/ml tetracycline.

To that end, total DNA was purified from the cells. The DNA obtained was analyzed by means of an agarose gel which in this case results in the appearance of bands that can be easily identified when comparing to the DNA preparation obtained from parental strain 6314 (FIG. 4C).

Example 6

Analysis of the Mutant Strains Obtained by Transformation by Means of Transposition Example 6.1

Analysis of the Mutant Strains Obtained by Transformation by Means of Transposition of Plasmid pTC3

Different transformant clones obtained by electroporation with plasmid TC3 were analyzed both by Southern blot and by direct sequencing of the genomic DNA to show that the tetracycline-resistant mutants were the result of the presence of the transposon insertion in the bacterial chromosome.

To ensure that all the clones obtained were bearing a single transposon insertion and these insertions were not remobilized after several generations, a Southern blot of the genomic DNA of a clone obtained by means of plasmid pTC3 named 232TC3hlyC was performed. This clone was so called because the sequencing results indicated that the transposon had been inserted in the coding sequence of the hlyC gene (base 843448 of the genome of strain 232, GenBank AE017332.1). To that end, both the genomic DNA of strain 232 and that of strain 232TC3hlyC were digested with restriction enzymes EcoRI and EcoRV. The resulting fragments were separated in a 0.7% agarose gel and were transferred to a nylon membrane. A probe was generated with oligonucleotides, SondaTet-5 (ATG AGT GGA TCC ATG AAA ATT ATT AAT ATT G) (SEQ ID NO: 44) and SondaTet-3 (CTA AGT TAT TTT ATT GAA CAT ATA TCG TAC TTT ATC) (SEQ ID NO: 45), by means of a PCR reaction with digoxigenin-labeled dUTP using plasmid pTC3 as a template. The probe recognizes the tetracycline resistance gene sequence TetM so that the regions of the genome where insertion of the transposon occurred (FIG. 5A) were detected in the Southern blot. The number and size of the bands coincided with those theoretically expected, indicating that the mutants obtained by this method and such vectors have a single copy of transposon insertion and that said insertion is kept stable after several generations.

Example 6.2

Analysis of the Mutant Strains Obtained by Transformation by Means of Transposition of Plasmid pTC3C, pTC3L and pTC3T Several mutants originated from each transposon were selected and called 6314Cc1, 232Cc6, 232Lc2, 232Tc2. As mentioned previously, two mutants with the plasmid designed for cytosolic expression (one, 6314Cc1, for strain 6314 and another, 232Cc6, for strain 232) were selected whereas the versions designed to be localized in the membrane have only been exemplified on strain 232 such as mutant 232Lc2 from plasmid pTC3L and mutant 232Tc2 from pTC3T.

The insertion points of the cytosolic version transposons (pTC3C) in the bacterial chromosome were determined by direct genomic DNA sequencing. Referring to the genome of strain 232 (GenBank AE017332.1) the transposon in clone 6314Cc1 was inserted in base 224547 whereas the transposon in clone 232Cc6 was inserted in base 569253.

To identify the presence of PCV2 capsid protein and to quantify it in the strains of Mhyo obtained (232Lc2, 232Cc6, 232Tc2 and 6314Cc1), a commercial kit (Ingenasa) which allows detecting and quantifying said antigen by means of on-plate immunodetection (ELISA) was used. The protein extracts were obtained after concentrating the cultures in exponential phase of each strain 100× and lysing the cells obtained in PBS and Triton® X-100 at a final concentration of 0.1% (v/v). The results were positive indicating that all the tested strains and plasmids express the proteins coded by ORF2 or ORF2v2 to a greater or lesser amount (FIG. 5B).

The strains with the version from plasmid pTC3C were also analyzed by means of denaturing polyacrylamide gel electrophoresis and Western-blot (FIG. 5C). Bands of the same molecular weight as PCV2 capsid protein were detected. Interestingly, there was no proteolytic degradation band, a common problem in the recombinant protein expression. All this suggests that PCV2 capsid protein expressed in Mhyo in a recombinant manner can be a good antigen for formulating a polyvalent vaccine. Likewise, it is confirmed that Mhyo is a good host for expressing recombinant proteins.

Example 7

Vaccination Assays

Example 7.1

Vaccination and Challenge with PCV2

It was tested the efficacy of vaccines containing transformed strains of Mhyo prepared according to the method of the invention, wherein said strains expressed PCV2 circovirus capsid protein in their cytosol, and the animals were challenged with a pathogenic strain of PCV2.

The responses assessed were the immunological response against Mhyo and against PCV2 determined by means of ELISA and the PCV2 viral DNA load in the serum of the animals.

For the test 72 pigs of 28 days of age were selected, they were randomly divided into 6 groups of 12 animals each.

Said efficacy was tested according to a $2^2$ factorial design with four groups of animals, in which the factors to be assessed were the transformed strains of Mhyo and the vaccination regimen. To that end vaccines containing strains 6314Cc1 or 232Cc6 were tested, and the animals were vaccinated following a single-dose regimen or revaccination regimen with an additional dose.

The assay groups performed are shown in Table II:

TABLE II

| Group | Revaccination | Strain |
|---|---|---|
| 1 | No | 6314Cc1 |
| 2 | Yes | 6314Cc1 |
| 3 | No | 232Cc6 |
| 4 | Yes | 232Cc6 |

Additionally, two groups of animals were incorporated in the study: a non-vaccinated but infected group (group 5), and a non-vaccinated and non-infected group (group 6).

The vaccines comprised the mutant strains of Mhyo inactivated by means of a non-ionic surfactant and a W/O/W-type emulsion as an adjuvant, and were administered intramuscularly on the neck of the animal.

The vaccination regimen consisted of administering a dose of 2 ml of vaccine at study day 0 to all the animals which were not part of the control groups, and half of the animals were revaccinated 14 days after first dose.

The animals in groups 5 and 6 received 2 ml of PBS as placebo both on the first day and on the $14^{th}$ day.

To prepare the antigens for the vaccines, transformed strains of Mhyo were grown in Friis medium with 0.5 μg/ml of tetracycline at a temperature of 37° C. under shaking between 100 and 200 rpm until a change in color due to a change in pH of the culture medium was observed.

The cultures were centrifuged and washed twice with PBS to obtain a 30-times concentrated culture. The antigen corresponding to transformed Mhyo strain 6314Cc1 had a titer of 9.2 color changing units/ml (CCU/ml $\log_{10}$) and the antigen corresponding to transformed Mhyo strain 232Cc6 has a titer of 9.45 CCU/ml $\log_{10}$. PCV2 capsid protein production was confirmed by means of ELISA (Ingezim PCV DAS, Ingenasa, Spain). The total protein of each antigen was 373 mg/I and 350.2 mg/I, respectively, determined by the Coomassie blue method.

The antigens were inactivated with a non-ionic surfactant and a W/O/W-type emulsion, such as Montanide® ISA 201 product (SEPPIC, France) in a ratio of 50:50 weight/weight, for example, was used as an adjuvant.

Blood samples were collected from the animals the day before the vaccination (day −1), day 13 (the day before revaccination), day 27 (before infection), and on day 7, 14, and 21 after the infection, corresponding respectively to day 35, 42 and 49 of the study.

Serum was obtained for determining the immunological response against PCV2 by means of the PCV2 Antibody ELISA test kit (Biocheck, The Netherlands) and against Mhyo by means of CIVTEST SUIS Myo (Hipra, Girona-Amer, Spain); and also for PCV2 viremia analysis.

The serum samples were obtained on days −1, 13 and 27 and, since they were expected to be negative, they were analyzed by standard PCR such as described, for example, in Quintana et al., Veterinary Record, 2001, 149, 357-361, whereas the samples collected on days 7 and 14 after infection were analyzed by quantitative PCR, as described, for example, in Olvera et al., J. Virol. Meth., 2004, 10 117, 75-80.

The animals from groups 1 to 5 were infected intranasally with 2 ml (5.66 $CCID_{50}$/ml $\log_{10}$) of a virulent wild type strain of PCV2 (Sp-107-54-13 PCV2, Fort et al., Vet. Immunol. Immunopathol., 2010, 137, 226-234) 28 days after the administration of the first dose of the vaccine. The animals from group 6 received 2 ml of PBS intranasally as placebo. The animals were euthanized on day 49 of the study, i.e., 21 days after infection.

During the completely blind, randomized infection-vaccination trial, the animals were housed in rooms with biosafety level 3. The group 6 was placed in a separate room to prevent cross-infections and was therefore the only group which was unblinded for the staff responsible of taking care of the animals.

Taking into account that the animals had anti-PCV2 maternal antibodies, the groups were treated in blocks with relation to this parameter to prevent initial differences among the groups.

The primary parameter for evaluating the efficacy of PCV2 infection was the reduction of PCV2 viremia determined by quantitative PCR.

The primary parameter for determining the efficacy with relation to Mhyo was the sero-conversion analyzed by ELISA.

Serological response to Mhyo is shown in FIG. 6. The four test vaccines promoted a significant sero-conversion compared with the non-vaccinated groups (groups 5 and 6) from day 13 of the study onwards.

After PCV2 infection, the vaccinated groups showed a greater immunological response with relation to the non-vaccinated but infected group on day 14 after infection and also on day 21 after infection with the exception of group 4.

The non-vaccinated and non-infected group showed the normal drop of anti-PCV2 maternal antibodies with a significant difference with the non-vaccinated and infected group on day 21 after infection.

No clinical signs associated with PCV2 infections were observed. PCV2 test models are normally sub-clinical models, and the key parameter for determining the vaccine efficacy is viremia reduction.

All the animals were negative with respect to PCV2 according to the analysis performed by standard PCR before infection. FIG. 8 shows the genomic copies of PCV2 which were quantified by real time by PCR 7 and 14 days after infection. No genomic copies of PCV2 were detected in the serum samples of the non-vaccinated and non-infected group.

PCV2 viremia was significantly lower in the vaccinated groups compared with the non-vaccinated but infected group on day 14 after infection.

The results of this study indicate that the strains of Mhyo transformed by means of the method of the invention and expressing the PCV2 capsid protein generate at the same time a significant immunological response against Mhyo and a porcine circovirus type 2 (PCV2).

The differential immunological response against PCV2 in vaccinated animals was clear on day 14 after infection, once PCV2 infection had been established, as inferred from the PCV2 viremia which is observed in the non-vaccinated and infected group (group 5).

Contrary to what happened with Mhyo, the presence of anti-PCV2 maternal antibodies prevented vaccine immunogenicity evaluation in the absence of an experimental infection.

Since the clinical signs corresponding to macroscopic lesions due to PCV2 infection cannot be reproduced in an experimental model, the result of PCV2 infection was assessed in terms of viremia by quantitative PCR and the vaccine efficacy was shown by means of viremia reduction. This reduction was observed for the four test vaccines 14 days after infection once the viremia reaches its highest level.

Therefore, the transformed strains of Mhyo expressing the PCV2 protein capsid can be used in vaccines against infections caused by Mhyo and by porcine circovirus type 2 (PCV2) at the same time.

Example 7.2

Vaccination and Infection with PCV2 and Mhyo

It was tested the efficacy of a vaccine containing a transformed strain of Mhyo prepared according to the method of the invention, wherein said strain expressed PCV2 circovirus capsid protein in its cytosol. The animals were challenged with pathogenic strains of PCV2 and Mhyo.

The responses assessed were the PCV2 viral DNA load in the serum of the animals, the number of animals with PCV2 viremia, and Mhyo-like lesions in the lungs of animals.

For the test 36 pigs of 28 days of age were selected, they were randomly divided into 3 groups of 12 animals each.

Said efficacy was tested with a vaccine containing strain 6314Cc1. The animals of group 1 were vaccinated following a single-dose regimen. Additionally, two groups of animals were incorporated in the study: a non-vaccinated but infected group (group 2), and a non-vaccinated and non-infected group (group 3).

The vaccine comprised the mutant strain of Mhyo inactivated by means of a non-ionic surfactant and a W/O/W-type emulsion as an adjuvant, and was administered intramuscularly on the neck of the animal.

The vaccination regimen consisted of administering a dose of 2 ml of vaccine at study day 0 to all the animals which were not part of the control groups.

The animals in groups 2 and 3 received 2 ml of PBS as placebo.

To prepare the antigens for the vaccine, the transformed strain of Mhyo was grown in Friis medium with 0.5 μg/ml of tetracycline at a temperature of 37° C. under shaking between 100 and 200 rpm until a change in color due to a change in pH of the culture medium was observed.

The cultures were centrifuged and resuspended in PBS to obtain a 25-times concentrated culture. The antigen corresponding to transformed Mhyo strain 6314Cc1 had a titer of 9,325 color changing units/ml (CCU/ml $\log_{10}$). PCV2 capsid protein production was confirmed by means of ELISA (Ingezim PCV DAS, Ingenasa, Spain).

The antigens were inactivated with a non-ionic surfactant, and as adjuvant it was used a W/O/W-type emulsion, for example, the product Montanide® ISA 201 (SEPPIC, France) in a ratio of 50:50 weight/weight.

Blood samples were collected from the animals the day before the vaccination (day −1), on day 13, 21 and 27 after vaccination, and on day 7, 14, 21 and 28 after the infection, corresponding respectively to day 35, 42, 49 and 56 of the study.

Serum was obtained for determining PCV2 viremia by using quantitative PCR, as described, for example, in Olvera et al., already cited.

The animals from groups 1 and 2 were infected intranasally with 2 ml/animal (5.33 $CCID_{50}$/ml $\log_{10}$) of a virulent wild type strain of PCV2 (Sp-107-54-13 PCV2, Fort et al., Vet. Immunol. Immunopathol., 2010, 137, 226-234), and intratracheally with 10 ml/animal of the pathogenic strain Mhyo 3371 (7.325 CCU/ml $\log_{10}$) 28 days after the administration of the vaccine. The animals from group 3 received 2 ml of PBS intranasally and 10 ml PBS/animal intratracheally as placebo. The animals were euthanized on day 56 of the study, i.e., 28 days after infection, at that moment the presence of Mhyo-like lesions in the lungs of animals was assessed.

During the completely blind, randomized infection-vaccination trial, the animals were housed in rooms with biosafety level 3. The group 3 was placed in a separate room to prevent cross-infections and was therefore the only group which was unblinded for the staff responsible of taking care of the animals.

Taking into account that the animals had anti-PCV2 maternal antibodies, the groups were treated in blocks with relation to this parameter to prevent initial differences among the groups.

The primary parameter for evaluating the efficacy of PCV2 infection was the reduction of PCV2 viremia determined by quantitative PCR. The primary parameter for determining the efficacy with relation to Mhyo was the lung surface affected by Mhyo-like lesions.

All the animals were negative with respect to PCV2 according to the analysis performed by standard PCR before the experimental infection. FIG. 12 shows the genomic copies of PCV2 which were quantified by real time by PCR 7, 14, 21 and 28 days after infection. No genomic copies of PCV2 were detected in the serum samples of the non-vaccinated and non-infected group. PCV2 viremia was significantly lower in the vaccinated group compared with the non-vaccinated but infected group on days 14 and 21 after infection.

In FIG. 13 are shown the same results expressed as percentage of animals with viremia (positive in quantitative PCR).

In FIG. 14 it is shown the median of the percentage of lung surface affected by Mhyo-like lesions. It was observed that the affected lung surface in vaccinated animals was significantly lower than that of non-vaccinated but infected animals (group 2).

The results of this study led to the conclusion that the strain of Mhyo genetically transformed according to the method of the invention and expressing the PCV2 capsid protein, generated at the same time a significant reduction in the PCV2 viremia and in the Mhyo-like lesions in comparison with the non-vaccinated animals.

Consequently, the transformed strains of Mhyo expressing the PCV2 protein capsid can be used in vaccines against infections caused by Mhyo and by porcine circovirus type 2 (PCV2) at the same time.

Example 8

Tests of the Degree of Attenuation of Transformed Mutant Strains

Example 8.1

Testing the Degree of Attenuation of a Transformed Mutant Strain Bearing Transposon Insertion in Mhyo Hemolysin C Gene The degree of attenuation of a mutant strain of Mhyo obtained by transposition was determined in this test by means of assessing the ability of said strain to colonize the upper and lower respiratory tract of pigs.

The tested mutant strain, 232TC3hlyC, obtained in Example 4.5, shows transposon insertion in Mhyo hemolysin C gene (hlyC).

Pigs of 8 weeks of age were selected, they were randomly divided into 2 groups of 8 animals each, and each group was kept in separate rooms to prevent cross-infections.

The animals were sedated before being infected. A group of animals was infected intratracheally on day 0 with 10 ml of mutant strain 232TC3hlyC, and the other group with 10 ml of the parental strain 232 of Mhyo. The inoculums had a titer of 7 CCU/ml $log_{10}$. The animals were euthanized on day 28 of the study.

Nasal samples were collected on days −1 (the day before infection), 8, 15, 21 and 28 to perform a Mhyo analysis by nested PCR.

Bronchial samples were collected on day 28 days from euthanized animals to perform a Mhyo analysis also by nested PCR.

No animals bearing the genomic DNA of Mhyo were detected in the nasal samples collected throughout the course of the study. However, Mhyo wild type strain 232 was detected in 25% of the bronchial samples of the animals, whereas the detection rate was 0% for the transformed mutant strain.

This result suggests that the mutant strain 232TC3hlyC shows an attenuated behavior in comparison with the parental strain which it comes from, in relation to lower respiratory tract colonization; therefore it can be used as an attenuated candidate in a vaccine against Mhyo.

Example 8.2

Testing the Degree of Attenuation of a Transformed Mutant Strain Showing Inhibition of the Expression of Mhyo Hemolysin 159 Gene The degree of attenuation of the strain 6314POGAc4 obtained in Example 4.8 showing inhibition of the expression of Mhyo hemolysin 159 gene was determined in another test.

Pigs of 8 weeks of age were selected, they were randomly divided into 3 groups of 8 animals each and were kept in separate rooms to prevent cross-infections.

On day 0 of the test, the animals from group 1 were intratracheally inoculated with 10 ml of strain 6314POGAc4 with a concentration of 8 CCU/ml $log_{10}$, and the same amount of wild type parental strain 6314 was administered to the animals from group 2. The animals were sedated before being infected. Group 3 was the non-infected control group. The animals were euthanized on day 28 of the study.

Blood samples were collected the day before the infection (day −1), and on days 15 and 28. Mhyo serology was analyzed by means of CIVTEST *SUIS* Mhyo (Hipra-Amer-Girona-Spain). Nasal samples were collected on days −1, 8, 15, 21 and 28 to perform a Mhyo analysis by nested PCR.

Bronchial samples were collected on day 28 from euthanized animals to perform a Mhyo analysis also by nested PCR.

The macroscopic catarrhal bronchopneumonia lung lesions compatible with a Mhyo infection were rated. Each lung lobe was rated from 0 and 5 according to the proportion of tissue with lesions caused by Mhyo.

The contribution of each lung lobe to the total affected lung surface was calculated by applying the method described in Christensen et al., *Diseases of the respiratory system*. In: *Diseases of Swine*. $8^{th}$ Edition. Straw B. E., D'Allaire S., Mengeling W. L. and Taylor D. J. Iowa State University Press, Ames (Iowa) 1999, page 914.

FIG. 9 shows the serological response against Mhyo infection. It can be observed that only the wild type parental strain (group 2) showed sero-conversion 28 days after infection, with a significant difference with respect to group 1, infected with transformed mutant strain 6314POGAc4, and to the control group.

FIG. 10 shows that Mhyo was only detected in the nasal samples of group 2 21 and 28 days after infection. In the 8 animals of group 2 Mhyo was detected in the bronchial samples collected on day 28, whereas the number was significantly less in the group to which the transformed mutant strain of the invention was administered.

It can be observed in FIG. 11 that the macroscopic lung lesions caused by Mhyo were significantly higher in group 2, infected with the wild type parental strain, whereas the animals infected with the mutant strain of the invention showed smaller lesions comparable to those observed in the non-infected group.

Therefore, it can be concluded that the transformed mutant strain of the invention tested in this example shows a reduced ability to colonize the upper and lower respiratory tract and also a reduced capacity to cause PEP-associated lung lesions.

All this suggests that said transformed mutant strain can be used for preparing attenuated vaccines against PEP and Mhyo-associated pathologies.

The invention claimed is:

1. A method for preparing a mutant strain of *Mycoplasma hyopneumoniae* (Mhyo) comprising transforming a strain of Mhyo with a carrier vector comprising at least one exogenous DNA sequence, wherein the at least one exogenous DNA sequence is under the control of a DNA sequence of a promoter region of Mhyo, wherein the carrier vector is a replicative plasmid vector that comprises:

1) a DNA sequence comprising the oriC region of a strain of *Mycoplasma* sp., which is *Mycoplasma hyopneumoniae*, and 2) an exogenous DNA sequence comprising a marker gene and an additional exogenous DNA sequence, each of which are under the control of a DNA sequence of a promoter region of Mhyo, wherein a DNA sequence of a promoter region of Mhyo corresponds to a DNA segment comprising at least 50 base pairs located on the 5' side of a gene coding for a Mhyo protein, wherein a DNA sequence of a promoter region of Mhyo initiates or promotes the transcription of a Mhyo DNA sequence, and wherein the exogenous DNA sequence is stably introduced in the cytosol or in the genome of the strain of Mhyo.

2. The method according to claim 1, characterized in that the additional exogenous DNA sequence is selected from a resistance gene to an antibiotic, a gene coding for a recombinase, a gene coding for a transposase, a transposase target sequence, a DNA fragment from Mhyo, a gene coding for an antigenic component of a microorganism causing porcine diseases, and combinations thereof.

3. The method according to claim 1, characterized in that the exogenous DNA sequence comprising a marker gene is a resistance gene to an antibiotic and the additional exogenous DNA sequence is a gene coding for an antigenic component of a microorganism causing porcine diseases optionally combined with a gene coding for a Mhyo membrane protein, wherein the additional exogenous DNA sequence induces a protective response against diseases or pathological conditions caused by the microorganism.

4. The method according to claim 3, characterized in that the vector comprises an additional exogenous DNA sequence coding for a recombinant protein inducing a protective response against diseases or pathological conditions affecting pigs caused by a microorganism selected from *Actinobacillus* sp., *Brachyspira* sp., *Pasteurella multocida, Salmonella* sp., *Streptococcus* sp., *Isospora* sp., *Erysipelothrix rhusiopathiae, Leptospira* sp., *Staphylococcus* sp., *Haemophilus parasuis, Bordetella bronchiseptica, Clostridium* sp., *Mycoplasma* sp., *Lawsonia intracellularis, Escherichia coli*, porcine reproductive and respiratory syndrome virus, swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), and porcine circovirus.

5. The method according to claim 4, characterized in that the additional exogenous DNA sequence is selected from a DNA sequence coding for the capsid protein of porcine circovirus type 2 (PCV2), and a DNA sequence coding for a protein comprising the capsid protein of PCV2 additionally bearing MetSerGlySer (SEQ ID NO: 46) amino acids at the N- terminal end of said protein, wherein said additional exogenous DNA sequence coding for the PCV2 capsid protein is selected from SEQ ID NO: 3, SEQ ID NO: 4, and SEQ ID NO: 5.

6. The method according to claim 1, characterized in that the additional exogenous DNA sequence is a Mhyo gene in reverse orientation with respect to the promoter region of Mhyo.

7. The method according to claim 1, characterized in that the step of transforming the Mhyo is carried out by incubating the Mhyo in the presence of a salt containing divalent ions, exposure to a mixture of polyethylene glycol, or electroporation.

8. The method according to claim 7, characterized in that the step of transforming the Mhyo is carried out by electroporation.

9. The method according to claim 8, characterized in that before performing the electroporation, the Mhyo is suspended and incubated in an electroporation buffer with a divalent ion chelating agent.

10. A replicative plasmid vector, characterized in that it comprises:

1) a DNA sequence comprising the oriC region of a strain of *Mycoplasma* sp., which is *Mycoplasma hyopneumoniae*, and 2) an exogenous DNA sequence comprising a marker gene, and an additional exogenous DNA sequence, each of which are under the control of a DNA sequence of a promoter region of Mhyo, wherein a DNA sequence of a promoter region of Mhyo corresponds to a DNA segment comprising at least 50 base pairs located on the 5' side of a gene coding for a Mhyo protein, and wherein a DNA sequence of a promoter region of Mhyo initiates or promotes the transcription of a Mhyo DNA sequence.

11. The vector according to claim 10, characterized in that the additional exogenous DNA sequence coding for a recombinant protein inducing a protective response against diseases or pathological conditions affecting pigs caused by a microorganism selected from *Actinobacillus* sp., *Brachyspira* sp., *Pasteurella multocida, Salmonella* sp., *Streptococcus* sp., *Isospora* sp., *Erysipelothrix rhusiopathiae, Leptospira* sp., *Staphylococcus* sp., *Haemophilus parasuis, Bordetella bronchiseptica, Clostridium* sp., *Mycoplasma* sp., *Lawsonia intracellularis, Escherichia coli*, porcine reproductive and respiratory syndrome virus, swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), and porcine circovirus.

12. The vector according to claim 11, characterized in that the additional exogenous DNA sequence is selected from a DNA sequence coding for the capsid protein of porcine circovirus type 2 (PCV2), and a DNA sequence coding for a protein comprising the capsid protein of PCV2 additionally bearing MetSerGlySer (SEQ ID NO: 46) amino acids at the N-terminal end of said protein, wherein said additional exogenous DNA sequence coding for the PCV2 capsid protein is selected from SEQ ID NO: 3, SEQ ID NO: 4, and SEQ ID NO: 5.

13. A method of preparing a mutant strain of Mhyo, comprising transforming a strain of Mhyo with the vector of claim 10.

14. A mutant strain of Mhyo obtained by the method as defined in claim 4.

15. A mutant strain of Mhyo characterized in that it comprises at least one exogenous DNA sequence stably incorporated in the genome or in the cytosol thereof, wherein the mutant strain of Mhyo comprises the replicative plasmid vector of claim 10.

16. A vaccine for protecting pigs against porcine enzootic pneumonia caused by Mhyo, and optionally against another disease or additional pathological conditions affecting pigs, comprising an immunologically effective amount of the mutant strain of Mhyo as defined in claim 14, wherein the disease or pathological conditions affecting pigs are caused by a microorganism selected from *Actinobacillus* sp., *Brachyspira* sp., *Pasteurella multocida, Salmonella* sp., *Streptococcus* sp., *Isospora* sp., *Erysipelothrix rhusiopathiae, Leptospira* sp., *Staphylococcus* sp., *Haemophilus parasuis, Bordetella bronchiseptica, Clostridium* sp., *Mycoplasma* sp., *Lawsonia intracellularis, Escherichia coli*, porcine reproductive and respiratory syndrome virus, swine influenza virus, contagious gastroenteritis virus, porcine parvovirus, encephalomyocarditis virus, coronavirus, rotavirus, porcine circovirus, porcine periweaning failure to thrive syndrome agent, classical swine fever virus, African swine fever virus, calicivirus, and torque teno virus (TTV).

17. The vaccine according to claim 16, characterized in that it is combined with an additional vaccine or antigenic composition for preventing or treating pigs against diseases or pathological conditions caused by a microorganism selected from *Actinobacillus* sp., *Brachyspira* sp., *Pasteurella multocida, Salmonella* sp., *Streptococcus* sp., *Isospora* sp., *Erysipelothrix rhusiopathiae, Leptospira* sp., *Staphylococcus* sp., *Haemophilus parasuis, Bordetella bronchiseptica, Clostridium* sp., *Mycoplasma* sp., *Lawsonia intracellularis, Escherichia coli*, porcine reproductive and respiratory syndrome virus, swine influenza virus, contagious gastroenteritis virus, porcine parvovirus, encephalomyocarditis virus, coronavirus, rotavirus, porcine circovirus, porcine periweaning failure to thrive syndrome agent, classical swine fever virus, African swine fever virus, calicivirus, and torque teno virus (TTV).

18. A vaccination kit for vaccinating pigs against an infection or disease caused by Mhyo and optionally against another disease or pathological conditions caused by microorganisms affecting pigs, comprising a container comprising an immunologically effective amount of the mutant strain as defined in claim 14, wherein the disease or pathological conditions affecting pigs are caused by a microorganism selected from *Actinobacillus* sp., *Brachyspira* sp., *Pasteurella multocida, Salmonella* sp., *Streptococcus* sp.,*Isospora* sp., *Erysipelothrix rhusiopathiae, Leptospira* sp., *Staphylococcus* sp., *Haemophilus parasuis, Bordetella bronchiseptica, Clostridium* sp., *Mycoplasma*sp., *Lawsonia intracellularis, Escherichia coli*, porcine reproductive and respiratory syndrome virus, swine influenza virus, contagious gastroenteritis virus, porcine parvovirus, encephalomyocarditis virus, coronavirus, rotavirus, porcine circovirus, porcine periweaning failure to thrive syndrome agent, classical swine fever virus, African swine fever virus, calicivirus, and torque teno virus (TTV).

19. A method of treating porcine enzootic pneumonia caused by Mhyo and optionally another disease or additional pathological condition affecting pigs by administering a mutant strain ofMhyo according to claim 14, wherein the disease or pathological condition affecting pigs is caused by a microorganism selected from *Actinobacillus* sp., *Brachyspira* sp., *Pasteurella multocida, Salmonella* sp., *Streptococcus* sp., *Isospora* sp., *Erysipelothrix rhusiopathiae, Leptospira* sp., *Staphylococcus* sp., *Haemophilus parasuis, Bordetella bronchiseptica, Clostridium* sp., *Mycoplasma* sp., *Lawsonia intracellularis, Escherichia coli*, porcine reproductive and respiratory syndrome virus, swine influenza virus, contagious gastroenteritis virus, porcine parvovirus, encephalomyocarditis virus, coronavirus, rotavirus, porcine circovirus, porcine periweaning failure to thrive syndrome agent, classical swine fever virus, African swine fever virus, calicivirus, and torque teno virus (TTV).

20. The method according to claim 2, characterized in that the DNA fragment from Mhyo, has been reordered or recombined with one or several DNA fragments.

21. The method according to claim 1, characterized in that the promoter region of Mhyo comprises the promoter region of the gene of a Mhyo protein selected from the group consisting of P36 Mhyo protein, P46 Mhyo protein, P65 Mhyo protein, P76 Mhyo protein, P97 Mhyo protein, P102 Mhyo protein, P146 Mhyo protein, and P216 Mhyo protein.

22. The method according to claim 21, characterized in that the promoter region of Mhyo comprises the promoter region of the gene of P46 Mhyo protein.

23. The method according to claim 21, characterized in that the promoter region of Mhyo comprises the promoter region of the gene of P97 Mhyo protein.

24. The vector according to claim 10, characterized in that the promoter region of Mhyo comprises the promoter region of the gene of a Mhyo protein selected from the group consisting of P36 Mhyo protein, P46 Mhyo protein, P65 Mhyo protein, P76 Mhyo protein, P97 Mhyo protein, P102 Mhyo protein, P146 Mhyo protein, and P216 Mhyo protein.

25. The vector according to claim 24, characterized in that the promoter region of Mhyo comprises the promoter region of the gene of P46 Mhyo protein.

26. The vector according to claim 24, characterized in that the promoter region of Mhyo comprises the promoter region of the gene of P97 Mhyo protein.

27. A mutant strain of Mhyo obtained by the method as defined in claim 1.

28. A method for preparing a mutant strain of *Mycoplasma hyopneumoniae* (Mhyo) comprising transforming a strain of Mhyo with a transposon vector comprising:

1) a DNA sequence encoding a transposase,
2) an exogenous DNA sequence comprising a marker gene, and
3) and an additional exogenous DNA sequence, wherein at least one of the exogenous DNA sequences and the DNA sequence encoding the transposase are under the control of a DNA sequence of a promoter region of Mhyo, wherein the DNA sequence of the promoter region of Mhyo corresponds to a DNA segment comprising at least a50 base pairs located on the 5' side of a gene coding for a Mhyo protein, wherein the DNA sequence of the promoter region of Mhyo initiates or promotes the transcription of a Mhyo DNA sequence, and wherein the exogenous DNA sequence is stably introduced in the cytosol or in the genome of the strain of Mhyo.

29. The method according to claim 28, characterized in that the additional exogenous DNA sequence is selected from a resistance gene to an antibiotic, a gene coding for a recombinase, a gene coding for a transposase, a transposase target sequence, a DNA fragment from Mhyo, a gene coding for an antigenic component of a microorganism that induces a therapeutic or protective response against diseases or pathological conditions, and combinations thereof.

30. The method according to claim 28 characterized in that the exogenous DNA sequence comprising a marker gene is a resistance gene to an antibiotic and the additional exogenous DNA sequence is a gene coding for an antigenic component of a microorganism causing porcine diseases optionally combined with a gene coding for a Mhyo membrane protein, wherein the additional exogenous DNA sequence induces a protective response against diseases or pathological conditions caused by the microorganism.

31. The method according to claim 30, characterized in that the additional exogenous DNA sequence is a gene coding for a recombinant protein that induces a protective response against diseases or pathological conditions affecting pigs caused by a microorganism selected from *Actinobacillus* sp., *Brachyspira* sp *Pasteurella multocida, Salmonella* sp., *Streptococcus* sp., *Isospora* sp., *Erysipelothrix rhusiopathiae, Leptospira* sp., Staphylococcus sp., *Haemophilus parasuis, Bordetella bronchiseptica, Clostridium* sp., *Mycoplasma* sp., *Lawsonia intracellularis, Escherichia coli*, porcine reproductive and respiratory syndrome virus, swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), and porcine circovirus.

32. The method according to claim 28, characterized in that the additional exogenous DNA sequence comprises a sequence selected from the group consisting of SEQ ID NO: 3, SEQ ID NO: 4, and SEQ ID NO: 5, and optionally wherein the exogenous DNA sequence comprising the marker gene is flanked by loxP sequences.

33. The method according to claim 28, characterized in that the promoter region of Mhyo comprises the promoter region of the gene of a Mhyo protein selected from the group-consisting of P36 Mhyo protein, P46 Mhyo protein, P65 Mhyo protein, P76 Mhyo protein, P97 Mhyo protein, P102 Mhyo protein, P146 Mhyo protein, and P216 Mhyo protein.

34. The method according to claim 28, characterized in that the additional exogenous DNA sequence is a Mhyo gene in reverse orientation with respect to the promoter region of Mhyo.

35. A transposon vector, characterized in that it comprises:

1) a DNA sequence encoding a transposase,
2) an exogenous DNA sequence comprising a marker gene, and
3) an additional exogenous DNA sequence, wherein at least one of the exogenous DNA sequences and the DNA sequence encoding the transposase are under the control of a DNA sequence of a promoter region of Mhyo, wherein the DNA sequence of the promoter region of Mhyo corresponds to a DNA segment comprising at least 50 base pairs located on the 5' side of a gene coding for a Mhyo protein, and wherein the DNA sequence of the promoter region of Mhyo initiates or promotes the transcription of a Mhyo DNA sequence.

36. The transposon vector according to claim 35, characterized in that the additional exogenous DNA sequence is a gene coding for a recombinant protein that induces a protective response against diseases or pathological conditions affecting pigs caused by a microorganism selected from *Actinobacillus* sp., *Brachyspira* sp., *Pasteurella multocida, Salmonella* sp., *Streptococcus* sp., *Isospora* sp., *Erysipelothrix rhusiopathiae, Leptospira* sp., *Staphylococcus* sp., *Haemophilus parasuis, Bordetella bronchiseptica, Clostridium* sp., *Mycoplasma* sp., *Lawsonia intracellularis, Escherichia coli*, porcine reproductive and respiratory syndrome virus, swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), and porcine circovirus.

37. The transposon vector according to claim 35, characterized in that the additional exogenous DNA sequence is selected from the group consisting of SEQ ID NO: 3, SEQ ID NO: 4, and SEQ ID NO: 5, and optionally wherein the exogenous DNA sequence comprising the marker gene is flanked by loxP sequences.

38. The transposon vector according to claim 35, characterized in that the promoter region ofMhyo comprises the promoter region of the gene of a Mhyo protein selected from the group consisting of P36 Mhyo protein, P46 Mhyo protein, P65Mhyo protein, P76 Mhyo protein, P97 Mhyo protein, P102 Mhyo protein, P146 Mhyo protein, and P216 Mhyo protein.

39. A method of preparing a mutant strain of Mhyo, comprising transforming a strain of Mhyo with the transposon vector of claim 35.

40. A mutant strain of Mhyo obtained by the method as defined in claim 30.

41. The mutant strain of Mhyo according to claim 40, wherein the mutant strain is a strain identified by an accession number selected from DSM 26020, DSM 26027, DSM 26033, DSM 26034, and DSM 26049, as assigned by Leibniz-Institut DSMZ.

42. A vaccine for protecting pigs against porcine enzootic pneumonia caused by Mhyo, and optionally against another disease or additional pathological conditions affecting pigs, comprising an immunologically effective amount of the mutant strain of Mhyo as defined in claim 40.

43. A vaccination kit for vaccinating pigs against an infection or disease caused by Mhyo and optionally against another disease or pathological conditions caused by microorganisms affecting pigs, comprising a container comprising an immunologically effective amount of the mutant strain as defined in claim 40.

44. A method of treating porcine enzootic pneumonia caused by Mhyo and optionally another disease or additional pathological condition affecting pigs by administering a mutant strain of Mhyo according to claim 40.

45. A mutant strain of Mhyo obtained by the method as defined in claim 28.

46. A mutant strain of Mhyo characterized in that it comprises at least one exogenous DNA sequence stably incorporated in the genome or in the cytosol thereof, wherein the mutant strain of Mhyo comprises the transposon vector of claim 35.

* * * * *

SEQUENCE LISTING

```
<160> NUMBER OF SEQ ID NOS: 46

<210> SEQ ID NO 1
<211> LENGTH: 265
<212> TYPE: DNA
<213> ORGANISM: Mycoplasma hyopneumoniae

<400> SEQUENCE: 1

gaagactgat tagaaattta gaactattca aatctttcaa aaaagtggcc taaaaacaat      60

gataaaaaaa tttccaaact tttttgttgc aaaaaaaaaa aaaaaaagta taattttaat     120

tgtacaagtt aaataaattt ttcacttatc ttttttttatt ttgcaaaact tttaaaaaaa     180

ttagatatct aaattatatt atatgattga gaaaatgaaa aatttatttc ctagaaccaa     240

gataattgag gtttaaaata tgagt                                           265
```

<210> SEQ ID NO 2
<211> LENGTH: 263
<212> TYPE: DNA
<213> ORGANISM: Mycoplasma hyopneumoniae

<400> SEQUENCE: 2
ttgaatttgt attttccata atctaaaatt ttacattttt ttataacaat ttttaaaaat 60
taccctttaa tttatagtat ttttttattt tttagtctaa attataaaat tatcttgaat 120
tttatttgaa tttttataat ttagtactaa aaaatacaaa tattttttcc tattctaaga 180
aaaattcatt ttttaaaaaa aattgatttt tatagtataa tttatttgta taattgaatt 240
aacttgattt gaaagggaac aaa 263

<210> SEQ ID NO 3
<211> LENGTH: 699
<212> TYPE: DNA
<213> ORGANISM: Artificial
<220> FEATURE:
<223> OTHER INFORMATION: synthetic gene

<400> SEQUENCE: 3
atgacatatc caagaagaag atatagaaga agaagacata gaccaagatc acatttagga 60
caaattttaa gaagaagacc atgattagtt catccaagac atagatatag atgaagaaga 120
aaaaatggaa tttttaatac aagattatca agaacatttg gatatacagt taaaagaaca 180
acagttacaa caccatcatg agcagttgat atgatgagat ttaaaattga tgattttgtt 240
ccaccaggag gaggaacaaa taaaatttca attccatttg aatattatag aattagaaaa 300
gttaaagttg aattttgacc atgttcacca attacacaag gagatagagg agttggatca 360
acagcagtta ttttagatga taattttgtt acaaaagcaa cagcattaac atatgatcca 420
tatgttaatt attcatcaag acatacaatt ccacaaccat tttcatatca ttcaagatat 480
tttacaccaa aaccagtttt agattcaaca attgattatt ttcaaccaaa taataaaaga 540
aatcaattat gattaagatt acaaacatca ggaaatgttg atcatgttgg attaggaaca 600
gcatttgaaa attcaaaata tgatcaagat tataatatta gagttacaat gtatgttcaa 660
tttagagaat ttaatttaaa agatccacca ttagaacca 699

<210> SEQ ID NO 4
<211> LENGTH: 702
<212> TYPE: DNA
<213> ORGANISM: Artificial
<220> FEATURE:
<223> OTHER INFORMATION: synthetic gene

<400> SEQUENCE: 4
atgacatatc caagaagaag atatagaaga agaagacata gaccaagatc acatttagga 60
caaattttaa gaagaagacc atgattagtt catccaagac atagatatag atgaagaaga 120
aaaaatggaa tttttaatac aagattatca agaacatttg gatatacagt taaaagaaca 180
acagttacaa caccatcatg agcagttgat atgatgagat ttaaaattga tgattttgtt 240
ccaccaggag gaggaacaaa taaaatttca attccatttg aatattatag aattagaaaa 300
gttaaagttg aattttgacc atgttcacca attacacaag gagatagagg agttggatca 360
acagcagtta ttttagatga taattttgtt acaaaagcaa cagcattaac atatgatcca 420
tatgttaatt attcatcaag acatacaatt ccacaaccat tttcatatca ttcaagatat 480

-continued

```
tttacaccaa aaccagtttt agattcaaca attgattatt ttcaaccaaa taataaaaga    540

aatcaattat gattaagatt acaaacatca ggaaatgttg atcatgttgg attaggaaca    600

gcatttgaaa attcaaaata tgatcaagat tataatatta gagttacaat gtatgttcaa    660

tttagagaat ttaatttaaa agatccacca ttagaaccat aa                       702


<210> SEQ ID NO 5
<211> LENGTH: 992
<212> TYPE: DNA
<213> ORGANISM: Artificial
<220> FEATURE:
<223> OTHER INFORMATION: synthetic gene

<400> SEQUENCE: 5

actagtacta gagaagactg attagaaatt tagaactatt caaatctttc aaaaaagtgg     60

cctaaaaaca atgataaaaa aatttccaaa ctttttgtt gcaaaaaaaa aaaaaaaagt    120

ataattttaa ttgtacaagt taaataaatt tttcacttat cttttttat tttgcaaaac    180

ttttaaaaaa attagatatc taaattatat tatatgattg agaaaatgaa aaatttattt    240

cctagaacca agataattga ggtttaaaat atgagtggat ccatgacata tccaagaaga    300

agatatagaa gaagaagaca tagaccaaga tcacatttag gacaaatttt aagaagaaga    360

ccatgattag ttcatccaag acatagatat agatgaagaa gaaaaaaatgg aatttttaat    420

acaagattat caagaacatt tggatataca gttaaaagaa caacagttac aacaccatca    480

tgagcagttg atatgatgag atttaaaatt gatgattttg ttccaccagg aggaggaaca    540

aataaaattt caattccatt tgaatattat agaattagaa aagttaaagt tgaattttga    600

ccatgttcac caattacaca aggagataga ggagttggat caacagcagt tattttagat    660

gataattttg ttacaaaagc aacagcatta acatatgatc catatgttaa ttattcatca    720

agacatacaa ttccacaacc attttcatat cattcaagat attttacacc aaaaccagtt    780

ttagattcaa caattgatta ttttcaacca aataataaaa gaaatcaatt atgattaaga    840

ttacaaacat caggaaatgt tgatcatgtt ggattaggaa cagcatttga aaattcaaaa    900

tatgatcaag attataatat tagagttaca atgtatgttc aatttagaga atttaattta    960

aaagatccac cattagaacc ataagcggcc gc                                  992


<210> SEQ ID NO 6
<211> LENGTH: 233
<212> TYPE: PRT
<213> ORGANISM: Porcine circovirus type 2 (PCV2)

<400> SEQUENCE: 6

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Arg Thr Thr Val Thr Thr
    50                  55                  60

Pro Ser Trp Ala Val Asp Met Met Arg Phe Lys Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
```

```
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Gly Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230


<210> SEQ ID NO 7
<211> LENGTH: 26
<212> TYPE: DNA
<213> ORGANISM: Staphylococcus aureus

<400> SEQUENCE: 7

gataaagtcc gtataattgt gtaaaa                                            26


<210> SEQ ID NO 8
<211> LENGTH: 26
<212> TYPE: DNA
<213> ORGANISM: Staphylococcus aureus

<400> SEQUENCE: 8

ttttacacaa ttatacggac tttatc                                            26


<210> SEQ ID NO 9
<211> LENGTH: 33
<212> TYPE: DNA
<213> ORGANISM: Artificial
<220> FEATURE:
<223> OTHER INFORMATION: synthetic oligonucleotide

<400> SEQUENCE: 9

atgcgcggcc gcttatttat cagaaacagt tag                                    33


<210> SEQ ID NO 10
<211> LENGTH: 38
<212> TYPE: DNA
<213> ORGANISM: Artificial
<220> FEATURE:
<223> OTHER INFORMATION: synthetic oligonucleotide

<400> SEQUENCE: 10

agtcgggccc agcttgcgca tcattggatg atggattc                               38


<210> SEQ ID NO 11
<211> LENGTH: 29
<212> TYPE: DNA
<213> ORGANISM: Artificial
<220> FEATURE:
<223> OTHER INFORMATION: synthetic oligonucleotide

<400> SEQUENCE: 11
```

actgggatcc atgaatatag ttgaaaatg 29

<210> SEQ ID NO 12
<211> LENGTH: 27
<212> TYPE: DNA
<213> ORGANISM: Artificial
<220> FEATURE:
<223> OTHER INFORMATION: synthetic oligonucleotide

<400> SEQUENCE: 12
ggatgggccc agcttgcgca tcattgg 27

<210> SEQ ID NO 13
<211> LENGTH: 40
<212> TYPE: DNA
<213> ORGANISM: Artificial
<220> FEATURE:
<223> OTHER INFORMATION: synthetic oligonucleotide

<400> SEQUENCE: 13
gatctctaga tcgaggaaga ctgattagaa atttagaact 40

<210> SEQ ID NO 14
<211> LENGTH: 34
<212> TYPE: DNA
<213> ORGANISM: Artificial
<220> FEATURE:
<223> OTHER INFORMATION: synthetic oligonucleotide

<400> SEQUENCE: 14
gatcggatcc actcatattt taaacctcaa ttat 34

<210> SEQ ID NO 15
<211> LENGTH: 27
<212> TYPE: DNA
<213> ORGANISM: Artificial
<220> FEATURE:
<223> OTHER INFORMATION: synthetic oligonucleotide

<400> SEQUENCE: 15
actgactagt agcttgcgca tcattgg 27

<210> SEQ ID NO 16
<211> LENGTH: 43
<212> TYPE: DNA
<213> ORGANISM: Artificial
<220> FEATURE:
<223> OTHER INFORMATION: synthetic oligonucleotide

<400> SEQUENCE: 16
atgcagatct atgtccaatt tactgaccgt acaccaaaat ttg 43

<210> SEQ ID NO 17
<211> LENGTH: 37
<212> TYPE: DNA
<213> ORGANISM: Artificial
<220> FEATURE:
<223> OTHER INFORMATION: synthetic oligonucleotide

<400> SEQUENCE: 17
atgcgggccc ttaatcgcca tcttccagca ggcgcac 37

<210> SEQ ID NO 18
<211> LENGTH: 45
<212> TYPE: DNA

```
<213> ORGANISM: Artificial
<220> FEATURE:
<223> OTHER INFORMATION: synthetic oligonucleotide

<400> SEQUENCE: 18

tgttatcgat accgtcgatg cacctcgagc taagttattt tattg                 45


<210> SEQ ID NO 19
<211> LENGTH: 44
<212> TYPE: DNA
<213> ORGANISM: Artificial
<220> FEATURE:
<223> OTHER INFORMATION: synthetic oligonucleotide

<400> SEQUENCE: 19

agacatcgaa agcttgatta tgctgattgc attctttcaa tttg                  44


<210> SEQ ID NO 20
<211> LENGTH: 42
<212> TYPE: DNA
<213> ORGANISM: Artificial
<220> FEATURE:
<223> OTHER INFORMATION: synthetic oligonucleotide

<400> SEQUENCE: 20

agaggaatcc gatttattta tcagaaacag ttagtctttt cc                    42


<210> SEQ ID NO 21
<211> LENGTH: 58
<212> TYPE: DNA
<213> ORGANISM: Artificial
<220> FEATURE:
<223> OTHER INFORMATION: synthetic oligonucleotide

<400> SEQUENCE: 21

agactctaga actagtggat cccccgggcc cctcgaggaa gactgattag aaatttag    58


<210> SEQ ID NO 22
<211> LENGTH: 46
<212> TYPE: DNA
<213> ORGANISM: Artificial
<220> FEATURE:
<223> OTHER INFORMATION: synthetic oligonucleotide

<400> SEQUENCE: 22

agacgaattc gaattcctgc agggatccac tcatatttta aacctc                46


<210> SEQ ID NO 23
<211> LENGTH: 34
<212> TYPE: DNA
<213> ORGANISM: Artificial
<220> FEATURE:
<223> OTHER INFORMATION: synthetic oligonucleotide

<400> SEQUENCE: 23

catcgaattc acgaattagt gattctgcct tttc                             34


<210> SEQ ID NO 24
<211> LENGTH: 35
<212> TYPE: DNA
<213> ORGANISM: Artificial
<220> FEATURE:
<223> OTHER INFORMATION: synthetic oligonucleotide

<400> SEQUENCE: 24

catcgaattc attaaagttg attcggtgtt taatc                            35
```

<210> SEQ ID NO 25
<211> LENGTH: 35
<212> TYPE: DNA
<213> ORGANISM: Artificial
<220> FEATURE:
<223> OTHER INFORMATION: synthetic oligonucleotide

<400> SEQUENCE: 25
catgctgcag cccgggggat ccactagttc tagag 35

<210> SEQ ID NO 26
<211> LENGTH: 27
<212> TYPE: DNA
<213> ORGANISM: Artificial
<220> FEATURE:
<223> OTHER INFORMATION: synthetic oligonucleotide

<400> SEQUENCE: 26
gtacccaatt cgccctatag tgagtcg 27

<210> SEQ ID NO 27
<211> LENGTH: 30
<212> TYPE: DNA
<213> ORGANISM: Artificial
<220> FEATURE:
<223> OTHER INFORMATION: synthetic oligonucleotide

<400> SEQUENCE: 27
tcgaggaaga ctgattagaa atttagaact 30

<210> SEQ ID NO 28
<211> LENGTH: 40
<212> TYPE: DNA
<213> ORGANISM: Artificial
<220> FEATURE:
<223> OTHER INFORMATION: synthetic oligonucleotide

<400> SEQUENCE: 28
gatcgggccc tcgaggaaga ctgattagaa atttagaact 40

<210> SEQ ID NO 29
<211> LENGTH: 39
<212> TYPE: DNA
<213> ORGANISM: Artificial
<220> FEATURE:
<223> OTHER INFORMATION: synthetic oligonucleotide

<400> SEQUENCE: 29
gatcggatcc atgacccaag tacattttac actgaaaag 39

<210> SEQ ID NO 30
<211> LENGTH: 39
<212> TYPE: DNA
<213> ORGANISM: Artificial
<220> FEATURE:
<223> OTHER INFORMATION: synthetic oligonucleotide

<400> SEQUENCE: 30
gatcctcgag ggggggccct tttacacaat tatacggac 39

<210> SEQ ID NO 31
<211> LENGTH: 34
<212> TYPE: DNA
<213> ORGANISM: Artificial
<220> FEATURE:

<223> OTHER INFORMATION: synthetic oligonucleotide

<400> SEQUENCE: 31
gatcggatcc atgaaaatta ttaatattgg agtt 34

<210> SEQ ID NO 32
<211> LENGTH: 50
<212> TYPE: DNA
<213> ORGANISM: Artificial
<220> FEATURE:
<223> OTHER INFORMATION: synthetic oligonucleotide

<400> SEQUENCE: 32
gatcgctgca ggaattcgat atcaagctta tcgataccgt cgatgcacct 50

<210> SEQ ID NO 33
<211> LENGTH: 34
<212> TYPE: DNA
<213> ORGANISM: Artificial
<220> FEATURE:
<223> OTHER INFORMATION: sequence variant type loxP

<400> SEQUENCE: 33
ataacttcgt atagcataca ttatacgaac ggta 34

<210> SEQ ID NO 34
<211> LENGTH: 69
<212> TYPE: DNA
<213> ORGANISM: Artificial
<220> FEATURE:
<223> OTHER INFORMATION: synthetic oligonucleotide

<400> SEQUENCE: 34
gattaagggc ccataacttc gtataggata ctttatacga agttatgtcg accccctcga 60
ggaagactg 69

<210> SEQ ID NO 35
<211> LENGTH: 74
<212> TYPE: DNA
<213> ORGANISM: Artificial
<220> FEATURE:
<223> OTHER INFORMATION: synthetic oligonucleotide

<400> SEQUENCE: 35
gggactagtt acggttcgta taatgtatgc tatacgaagt tatctgcagg atatcaagct 60
tatcgatacc gtcg 74

<210> SEQ ID NO 36
<211> LENGTH: 34
<212> TYPE: DNA
<213> ORGANISM: Artificial
<220> FEATURE:
<223> OTHER INFORMATION: synthetic oligonucleotide

<400> SEQUENCE: 36
gtgtaagctt aaaaaccagg atgcacaaaa taac 34

<210> SEQ ID NO 37
<211> LENGTH: 34
<212> TYPE: DNA
<213> ORGANISM: Artificial
<220> FEATURE:
<223> OTHER INFORMATION: synthetic oligonucleotide

<400> SEQUENCE: 37
tgttgcggcc gctttaggca tcaggattat caac 34

<210> SEQ ID NO 38
<211> LENGTH: 33
<212> TYPE: DNA
<213> ORGANISM: Artificial
<220> FEATURE:
<223> OTHER INFORMATION: synthetic oligonucleotide

<400> SEQUENCE: 38
agacactagt ttgaatttgt attttccata atc 33

<210> SEQ ID NO 39
<211> LENGTH: 33
<212> TYPE: DNA
<213> ORGANISM: Artificial
<220> FEATURE:
<223> OTHER INFORMATION: synthetic oligonucleotide

<400> SEQUENCE: 39
agagggatcc tgtaattgtt gaagttgctg cct 33

<210> SEQ ID NO 40
<211> LENGTH: 33
<212> TYPE: DNA
<213> ORGANISM: Artificial
<220> FEATURE:
<223> OTHER INFORMATION: synthetic oligonucleotide

<400> SEQUENCE: 40
tgttgcggcc gcttatggtt ctaatggtgg atc 33

<210> SEQ ID NO 41
<211> LENGTH: 31
<212> TYPE: DNA
<213> ORGANISM: Artificial
<220> FEATURE:
<223> OTHER INFORMATION: synthetic oligonucleotide

<400> SEQUENCE: 41
gtgtggatcc atgacatatc caagaagaag a 31

<210> SEQ ID NO 42
<211> LENGTH: 44
<212> TYPE: DNA
<213> ORGANISM: Artificial
<220> FEATURE:
<223> OTHER INFORMATION: synthetic oligonucleotide

<400> SEQUENCE: 42
atcttcttct tggatatgtc atggcatcag gattatcaac atta 44

<210> SEQ ID NO 43
<211> LENGTH: 44
<212> TYPE: DNA
<213> ORGANISM: Artificial
<220> FEATURE:
<223> OTHER INFORMATION: synthetic oligonucleotide

<400> SEQUENCE: 43
taatgttgat aatcctgatg ccatgacata tccaagaaga agat 44

<210> SEQ ID NO 44
<211> LENGTH: 31
<212> TYPE: DNA

-continued

```
<213> ORGANISM: Artificial
<220> FEATURE:
<223> OTHER INFORMATION: synthetic oligonucleotide

<400> SEQUENCE: 44

atgagtggat ccatgaaaat tattaatatt g                                    31


<210> SEQ ID NO 45
<211> LENGTH: 36
<212> TYPE: DNA
<213> ORGANISM: Enterococcus faecalis

<400> SEQUENCE: 45

ctaagttatt ttattgaaca tatatcgtac tttatc                               36


<210> SEQ ID NO 46
<211> LENGTH: 4
<212> TYPE: PRT
<213> ORGANISM: Artificial
<220> FEATURE:
<223> OTHER INFORMATION: Synthetic peptide

<400> SEQUENCE: 46

Met Ser Gly Ser
1
```